(12) United States Patent
Malm et al.

(10) Patent No.: US 7,005,538 B1
(45) Date of Patent: Feb. 28, 2006

(54) THYROID RECEPTOR ANTAGONISTS FOR THE TREATMENT OF CARDIAC AND METABOLIC DISORDERS

(75) Inventors: Johan Malm, Korsangarvagen (SE); Chris Litten, Stubbestigen (SE); Theresa Apelqvist, Huddinge (SE); Asa Hedfors, Huddinge (SE); Peter Brandt, Solna (SE); Karin Edvinsson, Stockholm (SE); Sandra Gordon, Mariefred (SE)

(73) Assignee: Karo Bio AB, Huddinge (SE)

( * ) Notice: Subject to any disclaimer, the term of this patent is extended or adjusted under 35 U.S.C. 154(b) by 87 days.

(21) Appl. No.: 10/130,434

(22) PCT Filed: Nov. 16, 2000

(86) PCT No.: PCT/EP00/11554

§ 371 (c)(1),
(2), (4) Date: Aug. 28, 2002

(87) PCT Pub. No.: WO01/36365

PCT Pub. Date: May 25, 2001

(30) Foreign Application Priority Data

Nov. 17, 1999 (GB) .................................... 9927056

(51) Int. Cl.
*C07C 61/00* (2006.01)

(52) U.S. Cl. .................... 562/400; 562/405; 562/444; 562/465; 562/472

(58) Field of Classification Search ............... 562/465, 562/472, 444, 400, 405; 514/570, 563, 538

See application file for complete search history.

(56) References Cited

U.S. PATENT DOCUMENTS 3,586,713 A 6/1971 Buu-Hoietal
3,789,070 A 1/1974 Aldo

FOREIGN PATENT DOCUMENTS

| EP | 0257828 A | 2/1988 |
| EP | 0 512 352 A | 11/1992 |
| FR | 5 837 M | 11/1966 |
| WO | WO 97 28137 A | 8/1997 |

OTHER PUBLICATIONS

Bhalerao et al, Synthetic Communications, (1995), 25 (10, pp. 1433-1439, CA document No. 123:227752.*
The Journal of the Chemical Society, No. 3, 1961, pp. 2890-2902.
Chimica Therapeutica, Societe D'etudes De Chimie Therapeutique, FR., vol 2., No. 1m 1967, pp. 39-48.
Lacourciere, Gerard M.: "Selenium Is Mobilized In Vivo from Free Selenocysteine and Is Incorporated Specifically into Formate Dehydrogenase H and tRNA Nucleosides", Journal of Bacteriology, vol. 184, No. 7, pp. 1040-1946 (Apr., 2002).
"Brassica Vegetables Brassicaceae as paradigm" : From Website: http//www.nucycletherapy.com/minerals/selenium/brassica.htm, pp. 1-3 (printed Jan., 2005).
"Selenium Makes the News": From Website: http//www.medicinalfood news.com/vol01/isssue2/selenium.htm, pp. 1-2 (printed Jan., 2005).

* cited by examiner

Primary Examiner—Cecilia J. Tsang
Assistant Examiner—Hector M. Reyes
(74) Attorney, Agent, or Firm—Todd E. Garabedian; Wiggin and Dana LLP

(57) ABSTRACT

This invention relates to novel compounds which are thyroid receptor ligands, preferably antagonists, and to methods for using such compounds in the treatment of cardiac arrhythmias, thyrotoxicosis and subclinical hyperthyrodism.

10 Claims, No Drawings

THYROID RECEPTOR ANTAGONISTS FOR THE TREATMENT OF CARDIAC AND METABOLIC DISORDERS

FIELD OF THE INVENTION

This invention relates to novel compounds which are thyroid receptor ligands, preferably antagonists, and to methods for using such compounds in the treatment of cardiac arrhythmias, thyrotoxicosis and subclinical hyperthyrodism.

BACKGROUND OF THE INVENTION

Nuclear hormone receptors comprise a class of intracellular, mostly ligand-regulated transcription factors, which include receptors for thyroid hormones. Thyroid hormones exert profound effects on growth, development and homeostasis in mammals. They regulate important genes in intestinal, skeletal and cardiac muscles, liver and the central nervous system, and influence the overall metabolic rate, cholesterol and triglyceride levels, heart rate, and affect mood and overall sense of well being.

There are two major subtypes of the thyroid hormone receptor, TRα and TRβ, expressed from two different genes. Differential RNA processing results in the formation of at least two isoforms from each gene. The $TR\alpha_1$, $TR\beta_1$, and $TR\beta_2$ isoforms bind thyroid hormone and act as ligand-regulated transcription factors. The $TR\alpha_2$ isoform is prevalent in the pituitary and other parts of the central nervous system, does not bind thyroid hormones, and acts in many contexts as a transcriptional repressor. In adults, the $TR\beta_1$ isoform is the most prevalent form in most tissues, especially in the liver and muscle. The $TR\alpha_1$ isoform is also widely distributed, although its levels are generally lower than those of the $TR\beta_1$ isoform. A growing body of data suggests that many or most effects of thyroid hormones on the heart, and in particular on the heart rate and rhythm, are mediated through the $TR\alpha_1$ isoform, whereas most actions of the hormones on the liver, muscle and other tissues are mediated more through the β-forms of the receptor. It is believed that the α-isoform of the receptor is the major drive to heart rate for the following reasons: (i) tachycardia is very common in the syndrome of generalized resistance to thyroid hormone in which there are defective TRβ-isoforms, and consequently high circulating levels of $T_4$ and $T_3$; (ii) tachycardia was observed in the only described patient with a double deletion of the TRβ gene (Takeda et al, J. Clin. Endrocrinol. & Metab. 1992, Vol. 74, p. 49); (iii) a double knockout TRα gene (but not β-gene) in mice showed bradycardia and lengthening of action potential compared to control mice; (iv) western blot analysis of human myocardial TRs show presence of the $TR\alpha_1$, $TR\alpha_2$ and $TR\beta_2$ proteins, but not $TR\beta_1$.

If the indications above are correct, an α-selective thyroid hormone receptor antagonist that interacts selectively with the heart would offer an attractive alternative treatment of heart related disorders, such as atrial and ventricular arrhythmias.

Atrial fibrillation (AF) is the most common type of sustained arrhythmia encountered in primary care practice and is significantly more common in elderly patients, thus reflecting a reduction in the threshold for AF with age. Pharmacological treatment of AF involves the following types of anti-arrhythmic drugs according to Vaughan-Williams classification: (i) of class I such as disopyramide and flecainide (sodium channel blocker); (ii) of class III such as amiodarone (potassium channel blocker, prolongation of repolarization); (iii) of class IV such as verapamil and dilitazem (calcium channel blocker). Many patients are also subjected to electric cardioversions in order to convert atrial fibrillation into sinus rhythm. It should be noted that current therapies are associated with pro-arrhythmic risks and anti-arrhythmic agents often have insufficient efficacy partly because effective doses are limited by side-effects.

Ventricular arrhythmia, especially sustained ventricular tachycardia (VT) and ventricular fibrillation (VF) is the main cause of death associated with heart attack. Historically, three types of antiarrhythmic agents, class I agents, β-adrenergic blockers (class II), amiodarone and sotalol, appeared to offer the best scope for mortality reduction in patients with cardiac disease by preventing the occurrence of VT/VF.

The outcome of CAST (Cardiac Arrhythmia Supression Trial, *N. Engl. J. Med.*, 321 (1989) 406–412) and its successor SWORD (Survival With Oral D-sotatol trial, 1994) created much concern regarding the potential of class I agents and sotalol. It was found that class I agents did not decrease mortalities in patient groups at risk for sudden cardiac death. For some subsets of patients, class I agents even proved to increase mortality. The SWORD trial was stopped when sotalol proved to give higher death rate in patients, compared with the placebo. A consequence of these results is that the use of implantable defibrillators and surgical ablation have increased and that the trend in the industry has been towards the development of highly specific class III agents. Some of these channel blockers have been withdrawn from clinical development due to proarrhythmic effects and the subject remains under intensive debate. In this context it should be noted that amiodarone, despite its complex pharmacokinetics, mode of action (amiodarone is not regarded as a pure class III agent) and numerous side effects, is currently considered by many to be the most effective agent in the control of both atrial and ventricular arrhythmia.

Thyrotoxicosis is the clinical syndrome that results when tissues are exposed to elevated levels of circulating thyroid hormones, thyroxine (3,5,3',5'-tetraiodo-L-thyronine, or $T_4$) and triiodothyronine (3,5,3'-triiodo-L-thyronine, or $T_3$). Clinically, this state often manifests itself in weight loss, hypermetabolism, lowering of serum LDL levels, cardiac arrhythmias, heart failure, muscle weakness, bone loss in postmenopausal women, and anxiety. In most instances, thyrotoxicosis is due to hyperthyroidism, a term reserved for disorders characterized by overproduction of thyroid hormones by the thyroid gland. The ideal treatment of hyperthyroidism would be the elimination of its cause. This is however not possible in the more common diseases producing thyroid hypersecretion. At present, treatment of hyperthyroidism is directed to reduce overproduction of thyroid hormones by inhibiting their synthesis or release, or by ablating thyroid tissue with surgery or radioiodine.

Drugs inhibiting thyroid hormone synthesis, release or peripheral conversion of $T_4$ to $T_3$ include antithyroid drugs (thionamides), iodide, iodinated contrast agents, potassium perchlorate and glucocorticoids. The main action of antithyroid drugs such as methimazole (MMI), carbimazole, and propylthiouracil (PTU), is to inhibit the organification of iodide and coupling of iodotyrosines, thus blocking the synthesis of thyroid hormones. As they neither inhibit iodide transport or block the release of stored thyroid hormones, control of hyperthyroidism is not immediate and in most cases requires 2 to 6 weeks. Factors that determine the speed of restoration of euthyroidism include disease activity, initial levels of circulating thyroid hormones, and intrathyroidal hormone stores. Serious side effects are not common with antithyroid drugs. Agranulocytosis is the the most feared problem and has been observed with both MMI or PTU treatment. The elderly may be more susceptible to this side effect, but agranulocytosis can occur in any age group, although less frequently. Inorganic iodide given in pharmacological doses (as Lugol's solution or as saturated solution of potassium iodide, SSKI) decreases its own transport into the thyroid, thus inhibiting iodide organification (the Wolff-Chaikoff effect), and rapidly blocks the release of $T_4$ and $T_3$ from the gland. However, after a few days or weeks, its antithyroid action is lost, and thyrotoxicosis recurs or may worsen. Short-term iodide therapy is used to prepare patients for surgery, usually in combination with a thionamide drug. Iodide is also used in the management of severe thyrotoxicosis (thyroid storm), because of its ability to inhibit thyroid hormone release acutely. Perchlorate interferes with accumulation of iodide by the thyroid. Gastric irritation and toxic reactions limit the long-term use of perchlorate in the management of hyperthyroidism. Glucocorticoids in high doses inhibit the peripheral conversion of $T_4$ to $T_3$. In Graves' hyperthyroidism, glucocorticoids appear to decrease $T_4$ secretion by the thyroid, but the efficiency and duration of this effect is unknown. The aim of surgical treatment or radioiodine therapy of hyperthyroidism is to reduce the excessive secretion of thyroid hormones by removal or destruction of thyroid tissue. Subtotal or near-total thyroidectomy is performed in Graves' disease and toxic multinodular goiter. Restoration of euthyroidism before surgery is mandatory. The classical approach combines a course of thionamide treatment to restore and maintain euthyroidism, and the preoperative administration of iodide for approximately 10 days in order to induce involution of the gland. Propranolol and other beta-adrenergic antagonist drugs are useful in controlling tachycardia and other symptoms of sympathetic activation.

A high affinity ThR antagonist would in principle have the ability to restore euthyrodism quicker than any of the above agents, considered that its action is competitive for the ThR receptor. Such an agent could be used either alone or in combination with the above drugs, alternatively before an ablative treatment. It may also serve as a safer substitute for antithyroid drugs, especially in elderly patients at a high risk of agranulocytosis. Furthermore, hyperthyrodism can aggravate pre-existing heart disease and also lead to atrial fibrillation (AF), congestive heart failure, or worsening of angina pectoris. In an elderly patient, often with mild but prolonged elevation of plasma thyroid hormones, symptoms and signs of heart failure and complicating AF may dominate the clinical picture and mask the more classical endocrine manifestations of the disease.

DESCRIPTION OF THE INVENTION

In accordance with the present invention, compounds are provided which are thyroid receptor ligands, and have the general formula:

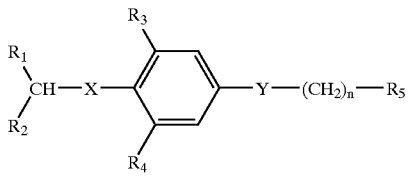

or a pharmaceutically acceptable salt thereof, wherein:
$R_1$ is selected from: $C_{5-10}$ aryl; $C_{5-10}$ heteroaryl; $C_{3-15}$ alkyl; $C_{4-15}$ alkenyl; $C_{3-15}$ alkynyl; and $C_{3-10}$ cycloalkyl, said aryl, heteroaryl, alkyl, alkenyl, alkynyl, cycloalkyl optionally being substituted with 1 to 3 groups of $R^a$;
$R_2$ is selected from: hydrogen; $C_{1-4}$ alkyl; $C_{2-4}$ alkenyl; $C_{2-4}$ alkynyl; and $C_{1-4}$ alkoxy; or a bioisosteric equivalent;
$R_1$ may be linked through the available carbons to $R_2$, thus forming a $C_4$–$C_8$ cycloalkyl, saturated or partially unsaturated, and optionally substituted with 1 to 3 groups of $R^a$;
X is selected from: of —O—; —S—; —SO—; $SO_2$—; —Se—; —Te—; —N($R^c$)—; and —S—S—;
$R_3$ and $R_4$ are the same or different and are selected from: halogen; $C_{1-4}$ alkyl; $C_{3-7}$ cycloalkyl; $C_{2-4}$ alkenyl; $C_{2-4}$ alkynyl; $C_{1-4}$ alkoxy; —$CF_3$; —$OCF_3$; —$OCF_2H$; —$SCH_3$; —$SCF_3$; and —COOH, or a bioisosteric equivalent; with the proviso that when $R_3$ is $C_{1-4}$ alkoxy; —$OCF_3$; —$OCF_2H$; —$SCH_3$; —$SCF_3$; or —COOH, then $R_4$ must be selected from: halogen; $C_{1-4}$ alkyl; $C_{2-4}$ alkenyl; $C_{2-4}$ alkynyl; $C_{3-7}$ cycloalkyl; and —$CF_3$;
n is an integer of 0, 1, 2 or 3;
Y is selected from: of —CO—; —O—; —S—; —CH($R^b$)—; and —N($R^c$)—;
$R_5$ is independently selected from:
  carboxylic acid (—$CO_2H$);
  phosphonic acid (—$PO(OH)_2$);
  phosphamic acid (—$PO(OH)NH_2$);
  sulphonic acid (—$SO_2OH$);
  α-keto carboxylic acid ($COCO_2H$);
  hydroxamic acid (—CONHOH);
  sulphonamide (—$SO_2NHR'$);
  sulphonamide (—$NHSO_2R'$), with the proviso that then Y is CO and n is 0;
  acylsulphonamide (—$CONHSO_2R'$) or (—$SO_2NHCOR'$);
  or any other possible bioisosteric equivalent of all the groups above;
$R^a$ represents a member selected from: hydrogen; halogen; —$CF_3$; $C_{1-4}$ alkyl; $C_{2-4}$ alkenyl; $C_{2-4}$ alkynyl; $C_{1-4}$ alkoxy; —SMe; —CN; —$NO_2$; and —$N(C_{0-4})_2$, or a bioisosteric equivalent;
$R^b$ represents a member selected from: hydrogen; halogen; —$CF_3$; $C_{1-4}$ alkyl; $C_{2-4}$ alkenyl; $C_{2-4}$ alkynyl; $C_{1-4}$ alkoxy; and —$(CH_2)_mOH$, where m is an integer between 0 and 4, or a bioisosteric equivalent;
$R^c$ represents a member selected from: hydrogen; $C_{1-4}$ alkyl; $C_{3-4}$ alkenyl; and $C_{3-4}$ alkynyl or a bioisosteric equivalent;
included for the variables above are all the possible stereoisomers thereof;
prodrug ester forms thereof; and radioactive forms thereof.

DETAILED DESCRIPTION OF THE INVENTION

The following definitions apply to the terms as used throughout this specification, unless otherwise limited in specific instances.

The term "thyroid receptor ligand" as used herein is intended to cover any chemical substance which binds to a thyroid receptor. The ligand may act as an antagonist, an agonist, a partial antagonist or a partial agonist.

The term "alkyl" as employed herein alone or as part of another group refers to acyclic straight or branched chain radical, containing 1 to 15 carbons, preferably 1 to 10 carbons in the normal chain, i.e. methyl, ethyl, propyl, propyl, butyl, pentyl, hexyl, heptyl, octyl, nonyl, decyl. Alkyl also refer to a radical where 1 to 6 hydrogens can be replaced by halogen through the available carbons. Alkyl also includes a straight or branched alkyl group which contains or is interrupted by a cycloalkane, preferable cyclopentane and cyclohexane, as exemplified below:

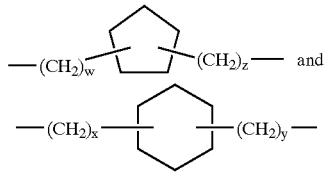

Wherein: when w and z is =1 to 9, the sum of w and z is not more than 10; and when x and y is =1 to 8, the sum of x and y is not more than 9.

The alkyl portions can be attached at any variable point of attachement to the cycloalkane. When a substituted alkyl is present, this refers to a straight or branched alkyl group as defined above, substituted with 1–3 groups of $R^a$ as defined with respect to each variable.

The term "alkenyl" as used herein by itself or as part of another group refers to straight or branched chain radicals of 2 to 15 carbons and at least one carbon to carbon double bond. Preferably one carbon to carbon double bond is present, and up to 5 carbon to carbon bonds may be present. Preferably 2 to 10 carbons are present in the normal chain radical, such as ethenyl, propenyl, butenyl, pentenyl, hexenyl, heptenyl, octenyl, decenyl, dodecenyl and the like. As described above with respect to the "alkyl", the straight or branched portion of the alkenyl group may be optionally substituted when a substituted alkenyl group is provided. The term "alkynyl" as used herein by itself or as part of another group refers to straight or branched chain radicals of 2 to 15 carbons and at least one carbon to carbon triple bond. Preferably one carbon to carbon triple bond is present, and up to 5 carbon to carbon triple bonds may be present. Preferably 2 to 10 carbons are present in the normal chain, such as ethynyl, propynyl, butynyl, pentynyl, hexynyl, heptynyl, octynyl, decynyl, dodecynyl and the like. As described above with respect to the "alkyl", the straight or branched portion of the alkynyl group may be optionally substituted when a substituted alkynyl group is provided.

The term "cycloalkyl" as employed herein alone or as part of another group refers to saturated cyclic hydrocarbon groups or partially unsaturated cyclic hydrocarbon groups, independently containing 1 to 2 carbon to carbon double bonds or carbon to carbon triple bonds. The cyclic hydrocarbon contain 3 to 10 carbons, including rings that are fused. It should also be understood that the present invention involves cycloalkyl rings where 1 to 2 carbons in the ring are replaced by either —O—, —S— or —N—, thus forming a saturated or partially saturated heterocycle. Preferred cycloalkyl groups include 3 to 6 carbons, such as cyclopropyl, cyclobutyl, cyclopentyl, cyclohexyl, cycloheptyl, cyclopentenyl, cyclohexenyl, which may be optionally substituted through available carbons as in the case of "alkyl".

The term "aryl" as employed herein alone or as part of another group refers to monocyclic and bicyclic aromatic groups, consisting of 5 to 10 carbons in the ring portion, including partially saturated rings such as indanyl and tetrahydronaphthyl. The preferred aryl groups are phenyl and naphthyl, which may be substituted with 0–3 groups selected from $R^a$.

The term "halogen" or "halo" as used herein alone or as part of another group, exemplified by "haloalkoxy", refers to chlorine, bromine, fluorine and iodine.

The term "alkoxy" refers to those groups of the designated carbon length in either a straight or branched configuration attached through an oxygen linkage and if two or more carbons are in the length, they may incude a double or a triple bond. Examples of such alkoxy groups are methoxy, ethoxy, propoxy, allyloxy, propargyloxy, butoxy, isobutoxy, tertiary butoxy, and the like. Alkoxy also refers to a radical where 1 to 3 hydrogens can be replaced by halogen through the available carbons, where the preferred group radical is —$OCF_3$.

The term "lower alkyl", "lower alkenyl" and "lower alkynyl" as employed herein alone or as part of another group includes both straight and branched chain hydrocarbons, containing 1 to 4 carbons, such as methyl, ethyl, vinyl, acetylene, n-propyl, i-propyl, butyl, t-butyl and the like. Lower alkyl also refers to a radical where 1 to 3 hydrogens can be replaced by halogen through the available carbons, where the preferred group radical is —$CF_3$.

The term "heteroaryl" or "heteroaromatic moiety" as used herein alone or as a part of another group refers to a group containing 5 to 10 atoms, where the aromatic ring includes 1 to 4 heteroatoms, such as nitrogen, oxygen or sulfur. Such rings may be fused to another aryl or heteroaryl ring, and includes possible N-oxides. The heteroaryl group may optionally be substituted by the available carbons with 0 to 3 substituents of $R^a$ and also include substitution with carbonyl, hydroxy, and/or carboxyl. When $R_5$ is selected from heterocycles it refers to mainly to 5 membered rings, containing at least one nitrogen, as exemplified and depicted below:

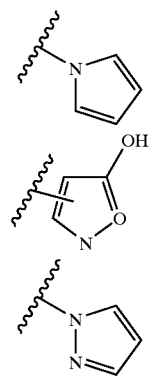

-continued

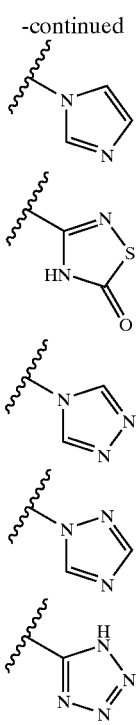

The term "phosphonic acid" refers to a phosphorus containing group of the structure:

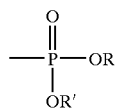

Wherein R and R' are independently selected from H or lower alkyl.

The term "bioisosteric equivalent" refers to compounds or groups that possess near equal molecular shapes and volumes, approximately the same distribution of electrons, and which exhibit similar physical and biological properties. Examples of such equivalents are: (i) fluorine vs. hydrogen, (ii) oxo vs. thia, (iii) hydroxyl vs. amide, (iv) carbonyl vs. oxime, (v) carboxylate vs. tetrazole. Examples of such bioisosteric replacements can be found in the literature and examples of such are given below:

1) Burger, A. *Relation of chemical structure and biological activity*.; in Medicinal Chemistry Third ed.; Burger, A., ed.; Wiley-Interscience: New York, 1970, pp. 64–80.
2) Burger, A.; "Isosterism and bioisosterism in drug design"; *Prog. Drug Res.* 1991, 37, 287–371.
3) Burger, A.; "Isosterism and bioanalogy in drug design"; *Med Chem. Res.* 1994, 4, 89–92.
4) Clark, R. D.; Ferguson, A. M.; Cramer, R. D.; "Bioisosterism and molecular diversity"; *Perspect. Drug Discovery Des.* 1998, 9/10/11, 213–224.
5) Koyanagi, T.; Haga, T.; "Bioisosterism in agrochemicals."; *ACS Symp. Ser.* 1995, 584, 15–24.
6) Kubinyi, H.; "Molecular similarities. Part 1. Chemical structure and biological activity"; *Pharm. Unserer Zeit* 1998, 27, 92–106.
7) Lipinski, C. A.; "Bioisosterism in drug design"; *Annu. Rep. Med Chem.* 1986, 21, 283–91.
8) Patani, G. A.; LaVoie, E. J.; "Bioisosterism: A rational approach in drug design"; *Chem. Rev. (Washington, D.C.)* 1996, 96, 3147–3176.
9) Soskic, V.; Joksimovic, J.; "Bioisosteric approach in the design of new dopaminergic/serotonergic ligands"; *Curr. Med. Chem.* 1998, 5, 493–512.
10) Thomber, C. W.; "Isosterism and molecular modification in drug design"; *Chem. Soc. Rev.* 1979, 8, 563–80.

The compounds of formula I can be present as salts, in particular "pharmaceutically acceptable salts". A compound having at least one acid group (for example —COOH) can form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or trilower alkylamine, for example ethyl, tertbutyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of formula I or their pharmaceutically acceptable salts, are also included. Preferred salts of the compounds of formula I include sodium, potassium and magnesium salts and pharmaceutically acceptable organic amines.

An acid center (for example —COOH) part in formula I can form "prodrug ester forms" known in the art such as pivaloyloxymethyl or dioxolenylmethyl. Such prodrug esters are described in standard references such as Chapter 31, written by Camille G. Wermuth et al., in "The Practice of Medicinal Chemistry", ed. C. G. Wermuth, Academic Press, 1996 (and the references contained therein).

Certain compounds of the invention can be "stereoisomers", which have one or more asymmetric centers and can exist in the form of racemates, single enantiomers, as individual diastereomers, with all possible isomers, and mixtures thereof, all of which are within the scope of the invention.

Preferred salts of the compounds of formula I include sodium, potassium and magnesium salts and pharmaceutically acceptable organic amines.

A preferred embodiment of formula I is when X is —O—.

Another preferred embodiment of formula I is when $R_2$ is selected from hydrogen and methyl; X is —O—; $R_3$ and $R_4$ are the same or different and are halogen, $C_{1-4}$ alkyl, $C_{2-4}$ alkenyl, $C_{2-4}$ alkynyl, or —$CF_3$; n is an integer of 0 or 1; Y is —CH($R^b$)—; $R_5$ is carboxylic acid (—$CO_2H$); $R^b$ is hydrogen.

Yet another preferred embodiment of formula I is when X is —O—; Y is —N($R^c$)—; n is an integer of 0, 1 and 2; $R_5$ is a carboxylic acid (—$CO_2H$) or an α-keto carboxylic acid ($COCO_2H$); $R^c$ is hydrogen.

Yet another preferred embodiment of formula I is when X is —O—; Y is —O—; n is an integer of 1 and 2; $R_5$ is a carboxylic acid (—$CO_2H$).

Yet another preferred embodiment of formula I is when X is —O—; Y is —CO—; n is 0; $R_5$ is a sulphonamide (—$NHSO_2R'$).

Yet another preferred embodiment of formula I is when $R_2$ is selected from hydrogen and methyl; X is —O—; $R_3$ is —COOH and $R_4$ is selected from: halogen; $C_{1-4}$ alkyl; $C_{2-4}$ alkenyl; $C_{2-4}$ alkynyl; and —$CF_3$; $R^b$ is hydrogen; $R^c$ is hydrogen.

The compounds of formula I may be prepared by the exemplary processes described in the following reaction schemes. Exemplary reagents and procedures for these reactions appear hereinafter and in the working Examples.

Compounds of formula I of the invention can be prepared using either method A, B or C as indicated in Scheme 1 below. In Scheme 1 (Method A, B or C) the phenol 1 is dissolved in a suitable solvent, treated with 1–5 molar equivalents of an appropriate base, such as potassium carbonate, cesium carbonate, potassium hydroxide, sodium hydride or triethylamine. The resulting anion is then O-alkylated with the appropriate halides R—Br, R-Cl or R-OMs. Other combinations of alkylating agents or bases may be employed and are known to those skilled in the art. The reaction mixture is stirred at room temperature or heated until the starting materials are consumed. After standard work-up, the ester function is removed by treatment with 3–6 molar equivalents of a base such as sodium hydroxide at room temperature, dissolved in a solvent such as methanol. The reaction mixture gives after acidification with hydrochloric acid a precipitate which is the end product 2 (Examples 1–20). In Examples 21–30 the end products 2 are further purified by column chromathography.

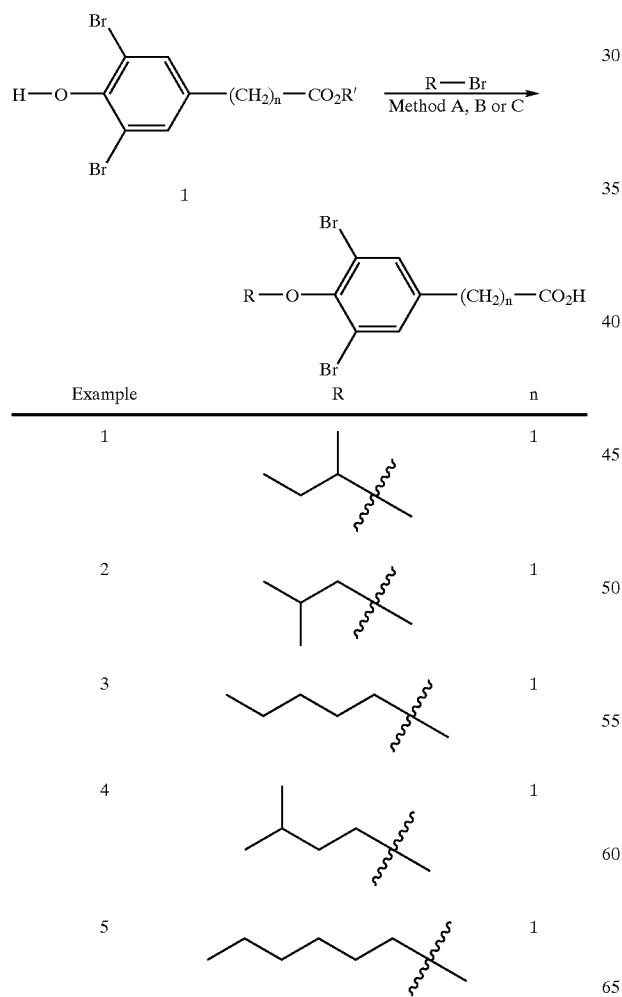

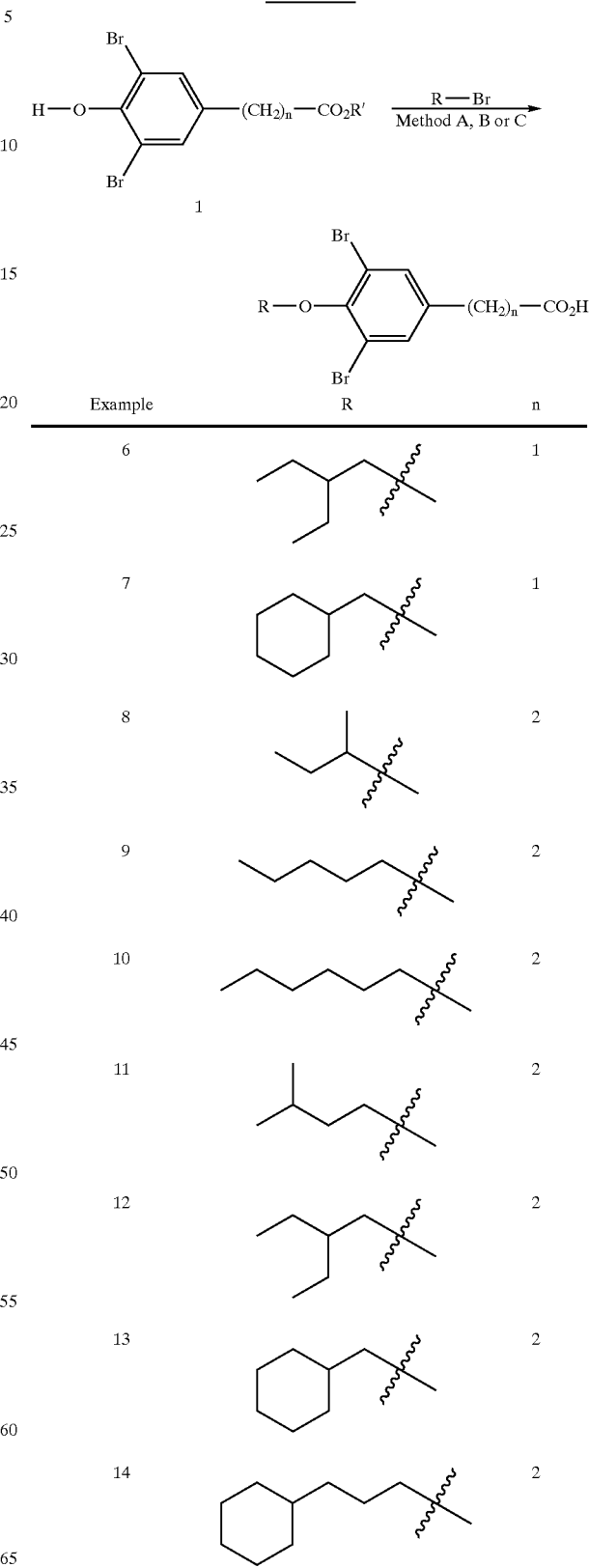

-continued
Scheme 1
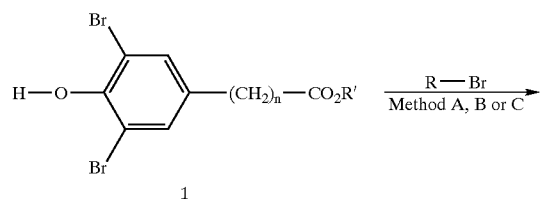
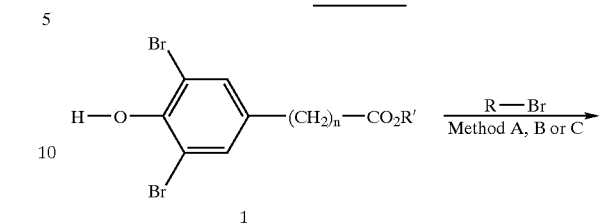
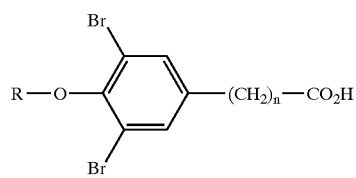
| Example | R | n |
|---|---|---|
| 15 | 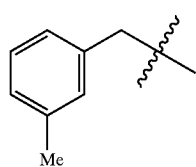 | 2 |
| 16 | 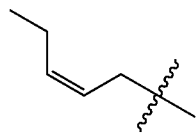 | 2 |
| 17 | 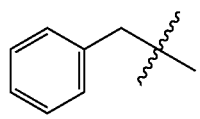 | 2 |
| 18 | 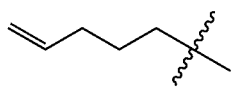 | 2 |
| 19 | 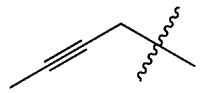 | 2 |
| 20 | 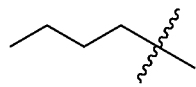 | 1 |
| 21 | 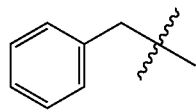 | 1 |
| 22 | 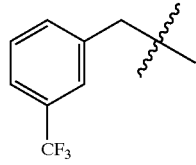 | 2 |
| Example | R | n |
|---|---|---|
| 23 | 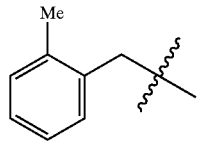 | 2 |
| 24 | 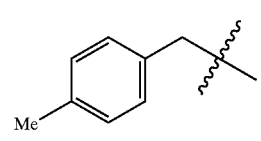 | 2 |
| 25 | 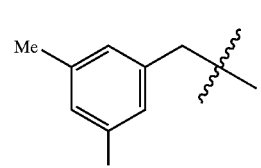 | 2 |
| 26 | 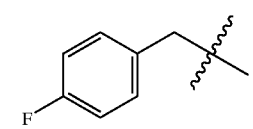 | 2 |
| 27 | 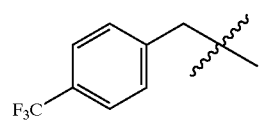 | 2 |
| 28 | 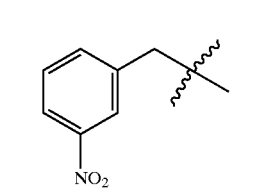 | 2 |
| 29 | | 2 |

Scheme 1

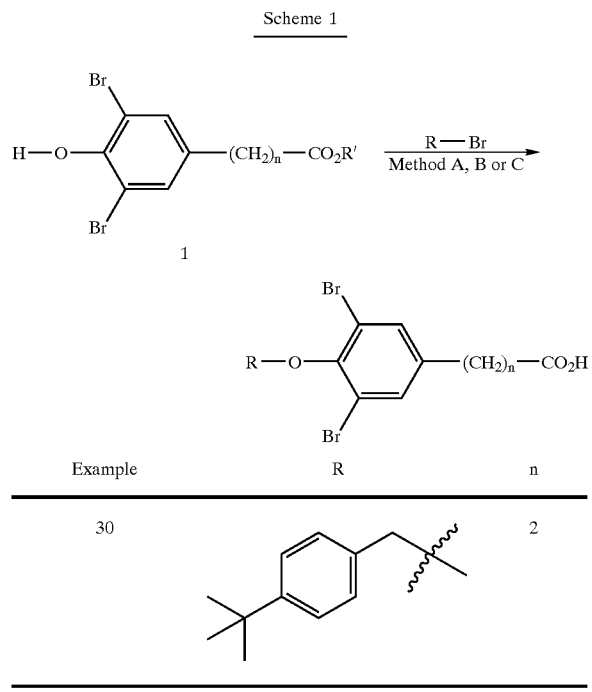

| Example | R | n |
|---|---|---|
| 30 | 4-tert-butylbenzyl | 2 |

Examples of compounds of formula I in which further variation at the $R_1$, $R_3$, $R_4$ and Y positions is introduced are shown in Scheme 2. A method similar as above is used for the O-alkylation step (Method D), but the preparations may be done in an automated fashion (Examples 36–100). After standard work-up, the ester function can be hydrolysed by 4 different methods (D1–D4) to give the end-products 4.

In the first method (D1), the ester is dissolved in methanol, sodium hydroxide is added and the mixture stirred at room temperature. After acidification with hydrochloric acid the product is extracted into ethyl acetate. In the second method (D2), the ester is dissolved in dry dichloromethane, potassium trimethylsilanolate is added and the reaction mixture is stirred at room temperature. After concentration, the residue is re-dissolved in methanol and neutralised on an SCX SPE column. In the third method (D3), the ester is dissolved in dry tetrahydrofuran, potassium trimethylsilanolate is added and the reaction mixture stirred at room temperature. The mixture is neutralised on an SCX SPE column. In the last method (D4), the ester is dissolved in tetrahydrofuran, lithium hydroxide is added and the reaction mixture stirred at room temperature. The mixture is neutralised on an SCX SPE column. In all methods, the final products are further purified on a silica SPE column.

Several other related methodologies exist for the hydrolysis of alkyl esters and are known to those skilled in the art. Furthermore, other protecting groups for the carboxylic acid can be employed, and their usage is known to those skilled in the art (references describing protecting group strategy include, for example, "Protecting Groups in Organic Chemistry", J. F. W. McOmie, Plenum Press, London, New York, 1973, and "Protective Groups in Organic Synthesis", T. W. Greene, Wiley, New York, 1984).

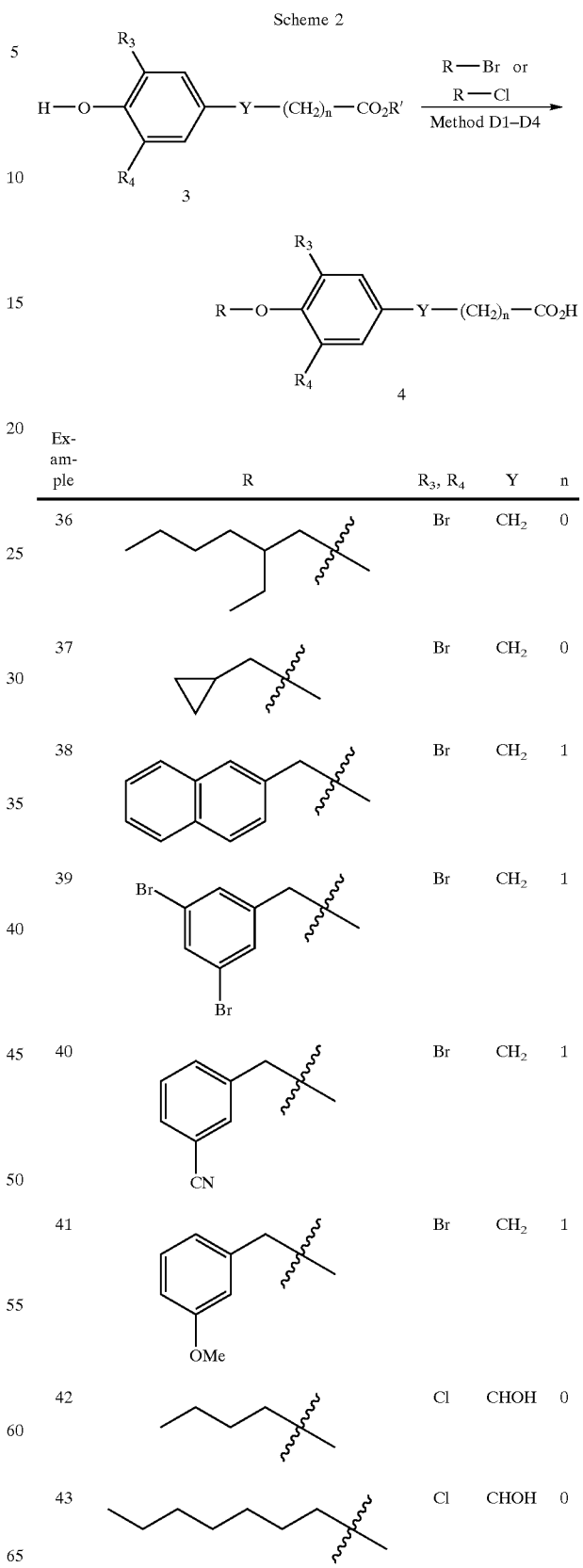

-continued
Scheme 2
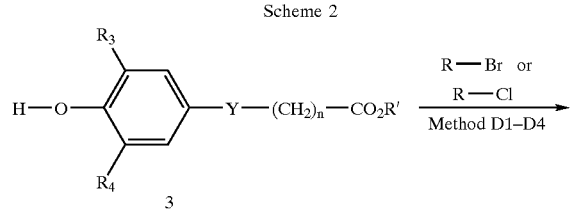
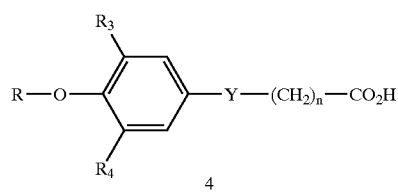
| Example | R | R₃, R₄ | Y | n |
|---|---|---|---|---|
| 44 | 3-bromobenzyl | Cl | CHOH | 0 |
| 45 | n-pentyl | Cl | C=O | 0 |
| 46 | n-octyl | Cl | C=O | 0 |
| 47 | 3-bromobenzyl | Cl | C=O | 0 |
| 48 | 3,5-dimethylbenzyl | Cl | C=O | 0 |
| 49 | 3-methoxybenzyl | Cl | C=O | 0 |
| 50 | n-pentyl | Me | CH₂ | 0 |
-continued
Scheme 2
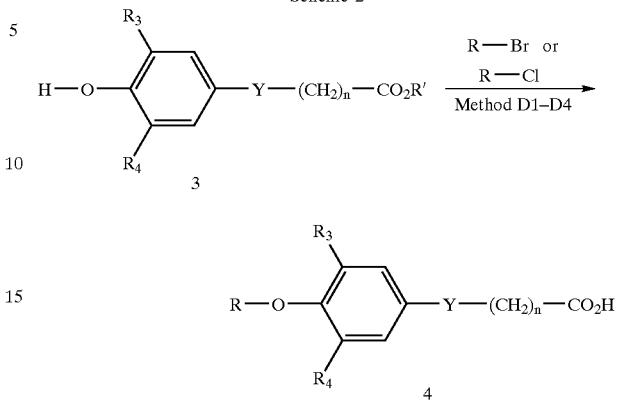
| Example | R | R₃, R₄ | Y | n |
|---|---|---|---|---|
| 51 | cyclohexylmethyl | Me | CH₂ | 0 |
| 52 | n-octyl | Me | CH₂ | 0 |
| 53 | 3-bromobenzyl | Me | CH₂ | 0 |
| 54 | 3,5-dimethylbenzyl | Me | CH₂ | 0 |
| 55 | 3-methoxybenzyl | Me | CH₂ | 0 |
| 56 | n-pentyl | Me | C=O | 0 |
| 57 | n-octyl | Me | C=O | 0 |
| 58 | 3-bromobenzyl | Me | C=O | 0 |

-continued

Scheme 2

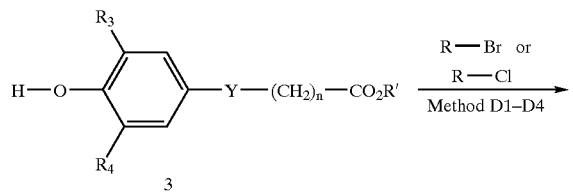

| Example | R | $R_3$, $R_4$ | Y | n |
|---|---|---|---|---|
| 59 | 3,5-dimethylbenzyl | Me | C=O | 0 |
| 60 | 3-methoxybenzyl | Me | C=O | 0 |
| 61 | 2-methylbutyl | i-Pr | C=O | 0 |
| 62 | 2-ethylhexyl | i-Pr | C=O | 0 |
| 63 | cyclohexylmethyl | i-Pr | C=O | 0 |
| 64 | n-heptyl | i-Pr | C=O | 0 |
| 65 | 3-bromobenzyl | i-Pr | C=O | 0 |

Further variations of the $R_3$ and $R_4$ groups are shown in Scheme 3, where $R_4$ is equal to a methoxy group and $R_3$ is a equal to a bromine. In the referred Examples 109 and 110 the same coupling procedures as above were employed.

Scheme 3

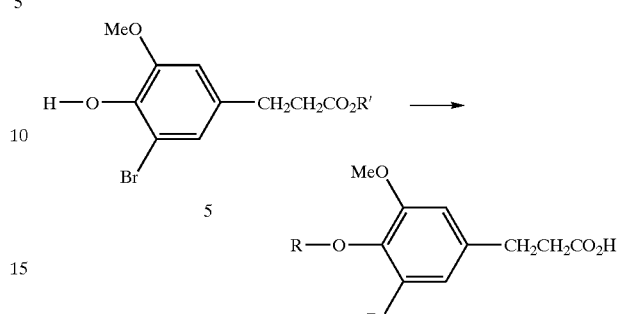

Scheme 4 depicts a synthesis of compounds of formula I in which —Y—$(CH_2)_n$—$R_5$ is an acylsulphonamide (when Y=CO, n=0 and $R_5$=—$NHSO_2R$).

In one procedure, 8 is mixed with a base such as N,N-diisopropylethylamine (DIEA) and the appropriate sulphonamide in a mixture of dichloromethane and dimethylformamide. Treatment of the mixture with a base and coupling reagent combinations such as benzotriazole-1-yl-oxy-tris-pyrrolidino phosphonium hexafluorophosphate (PyBOP) and 1-hydroxybenzotriazole hydrate (HOBt), gives after stirring at room temperature and subsequent mild acid treatment during work-up and purification by HPLC, the desired acylsulphonamides 9 (Example 31–33, 35).

Several other procedures for the preparation of acylsulphonamides can be employed. For example, a carboxylic acid, a coupling reagent such as 3-ethyl-1-[3-(dimethylamino)propyl]carbodiimide hydrochloride (EDCI), and a base such as dimethylaminopyridine (DMAP) and a sulphonamide in dichloromethane can be stirred at room temperature, to give an acylsulphonamide.

Scheme 4

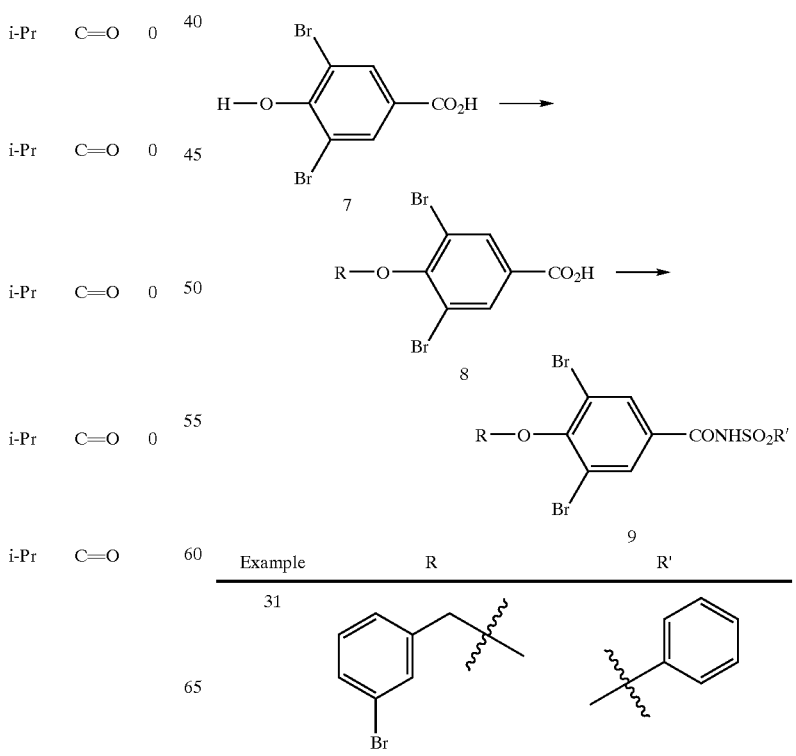

Scheme 4

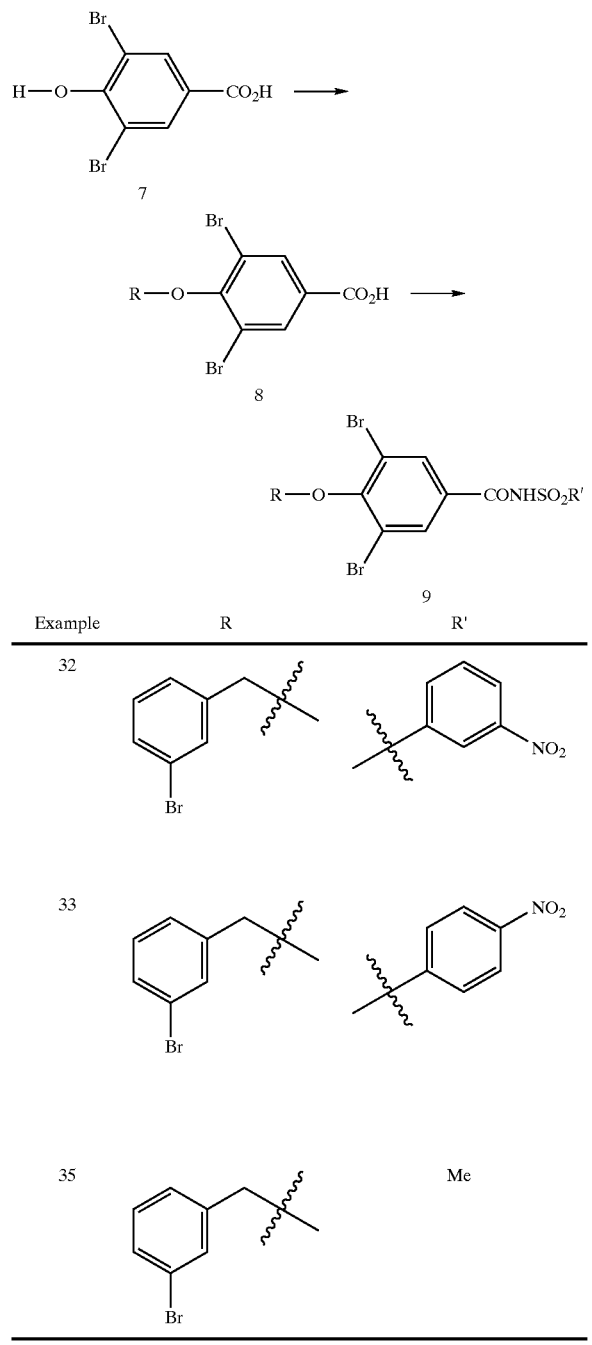

Additional examples of transformations of the Examples is shown in Scheme 5, where the nitro group of Example 33 is reduced to an amino group to give 10 (Example 34) by employing sodium dithionite. Several other reducing agents are known to those skilled in the art and the referred example should not be considered as limiting.

Scheme 5

Example 33 ⟶

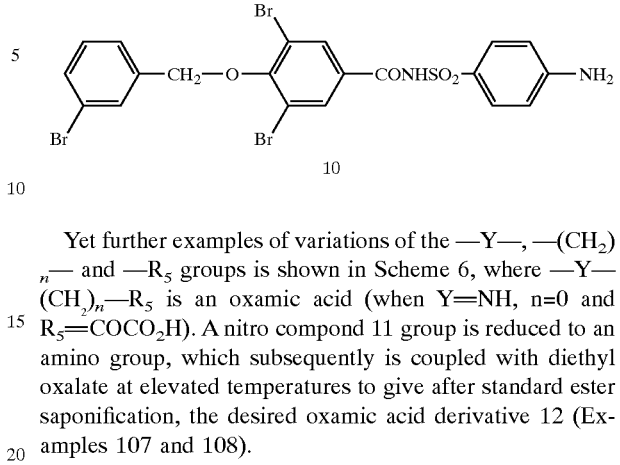

Yet further examples of variations of the —Y—, —(CH$_2$)$_n$— and —R$_5$ groups is shown in Scheme 6, where —Y—(CH$_2$)$_n$—R$_5$ is an oxamic acid (when Y=NH, n=0 and R$_5$=COCO$_2$H). A nitro compond 11 group is reduced to an amino group, which subsequently is coupled with diethyl oxalate at elevated temperatures to give after standard ester saponification, the desired oxamic acid derivative 12 (Examples 107 and 108).

Scheme 6

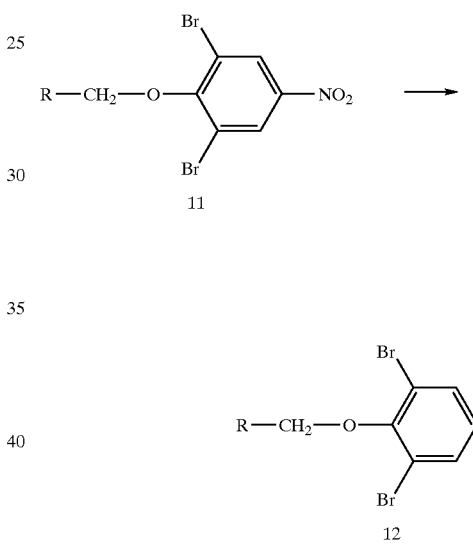

Examples where two O-alkylations are done in a consecutive order is depicted in Scheme 7. Following similar procedures as described above (Method D), methyl 3-(3,5-dibromo-4-hydroxyphenyl)propionate is reacted with 3-bromomethyl-phenyl acetate, hydrolyzed to give the intermediate 13 and then further reacted with the exemplified lower haloalkyls, to give 14 (Examples 101, 102 and 103). Other alternative combinations of starting phenols, halides and procedures can be employed and are obvious for those skilled in the art.

Scheme 7

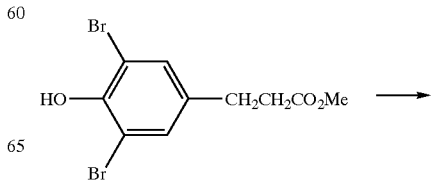

-continued

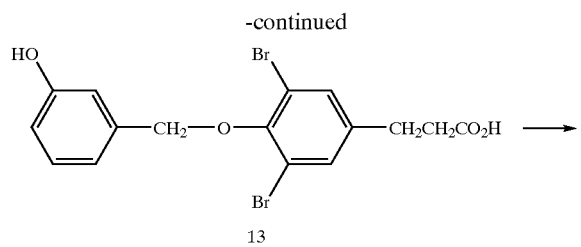

13

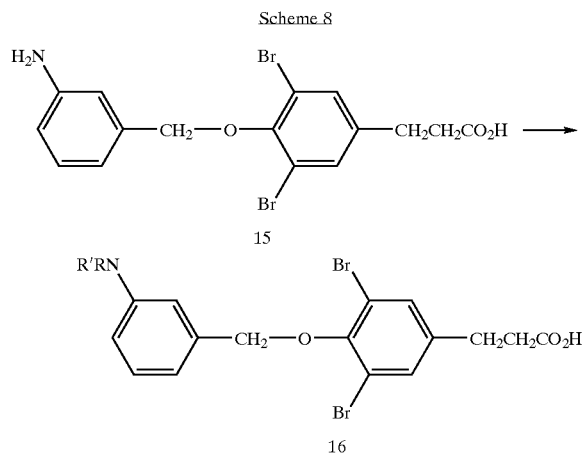

14

Example 101, R = Et
Example 102, R = Pr
Example 103, R = Bu

A similar strategy as above is exemplified and depicted in Scheme 8. Amino compound 15 (Example 104) can be further reacted with acetic acid under reductive conditions at different temperatures. Depending on temperature and reaction time, the mono or di-N-alkylated product is obtained. Many alternative procedures for the N-alkylation of aromatic amines can be employed and are obvious for those well skilled in the art.

Scheme 8

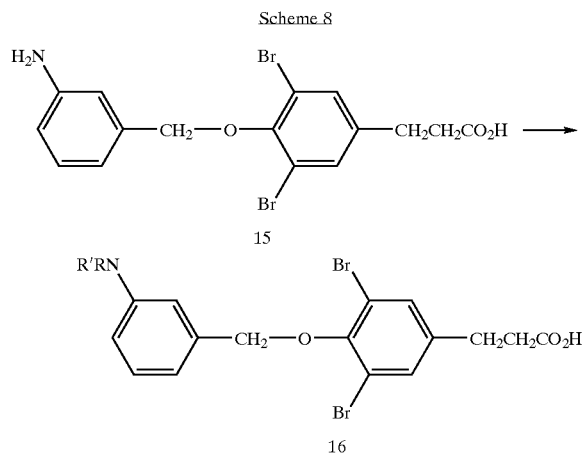

15

16

Example 105, R = Et, R' = H
Example 106, R = R' = Et

With respect to the above reaction scheme, although the various $R_1$, $R_2$, $R_3$, $R_4$, $R_5$, X, Y and n moieties are specifically defined, unless otherwise indicated, it is to be understood that $R_1$, $R_2$, $R_3$, $R_4$, $R_5$, X and Y may be any of the groups encompassed thereby and n may be 0, 1, 2, or 3.

Another aspect of the present invention refers to the use of a compound in medical therapy according to the formula below:

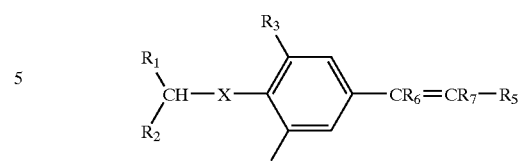

wherein:
$R_1$ is selected from: of $C_{5-10}$ aryl; $C_{5-10}$ heteroaryl; $C_{3-15}$ alkyl; $C_{4-15}$ alkenyl; $C_{3-15}$ alkynyl; and $C_{3-10}$ cycloalkyl, said aryl, heteroaryl, alkyl, alkenyl, alkynyl, cycloalkyl optionally being substituted with 1 to 3 groups of $R_a$;
$R_2$ is selected from: hydrogen; $C_{1-4}$ alkyl; $C_{2-4}$ alkenyl; $C_{2-4}$ alkynyl; and $C_{1-4}$ alkoxy, or a bioisosteric equivalent;
$R_1$ may be linked through the available carbons to $R_2$, thus forming a $C_4$–$C_8$ cycloalkyl, saturated or partially unsaturated, and optionally substituted with 1 to 3 groups of $R^a$;
X is selected from: —O—; —S—; —SO—; $SO_2$—; —Se—; —Te—; —N($R^c$)—; and —S—S—;
$R_3$ and $R_4$ are the same or different and are selected from: halogen; $C_{1-4}$ alkyl; $C_{3-7}$ cycloalkyl; $C_{2-4}$ alkenyl; $C_{2-4}$ alkynyl; $C_{1-4}$ alkoxy; —$CF_3$; —$OCF_3$; —$OCF_2H$; —$SCH_3$; —$SCF_3$; —COOH or a bioisosteric equivalent;
Y is selected from: —CO—; —O—; —S—; —CH(Rb)—; and —N($R^c$)—;
$R_5$ is independently selected from carboxylic acid (—$CO_2H$); phosphonic acid (—$PO(OH)_2$); phosphamic acid (—$PO(OH)NH_2$); sulphonic acid (—$SO_2OH$); α-keto carboxylic acid ($COCO_2H$); hydroxamic acid (—CONHOH); sulphonamide (—$SO_2NHR'$); sulphonamide (—$NHSO_2R'$); acylsulphonamide (—$CONHSO_2R'$) or (—$SO_2NHCOR'$) or any other possible bioisosteric equivalent of all the groups above;
$R_6$ and $R_7$ are the same or different and are selected from: hydrogen; halogen; —$CF_3$; $C_{1-4}$ alkyl; $C_{2-4}$ alkenyl; $C_{2-4}$ alkynyl; $C_{1-4}$ alkoxy; and —$(CH_2)_mOH$; where m is an integer between 1 and 4, or a bioisosteric equivalent;
$R^a$ is selected from: hydrogen; halogen; —$CF_3$; $C_{1-4}$ alkyl; $C_{2-4}$ alkenyl; $C_{2-4}$ alkynyl; $C_{1-4}$ alkoxy; —SMe; —CN; —$NO_2$; and —$N(C_{0-4})_2$, or a bioisosteric equivalent;
$R^b$ represents a member selected from: hydrogen; halogen; —$CF_3$; $C_{1-4}$ alkyl; $C_{2-4}$ alkenyl; $C_{2-4}$ alkynyl; $C_{1-4}$-alkoxy; and —$(CH_2)_mOH$, where m is an integer between 0 and 4, or a bioisosteric equivalent;
$R^c$ is selected from: hydrogen; $C_{1-4}$ alkyl; $C_{3-4}$ alkenyl; and $C_{3-4}$ alkynyl, or a bioisosteric equivalent;
or pharmaceutically acceptable salts thereof as well as included for the variables above are all the possible stereoisomers thereof; prodrug ester forms thereof; and radioactive forms thereof.

A preferred embodiment of this aspect of the present invention are the use of the compounds referred to above wherein:
$R_2$ is selected from hydrogen and methyl;
X is —O—;
$R_3$ and $R_4$ are the same or different and are selected from: halogen; $C_{1-4}$ alkoxy; $C_{1-4}$ alkyl; and —$CF_3$;
$R_5$ is a carboxylic acid (—$CO_2H$);
$R_6$ and $R_7$ is hydrogen.

A particularly preferred embodiment of this aspect of the present invention relates to, but not limited to the use of the following compounds:

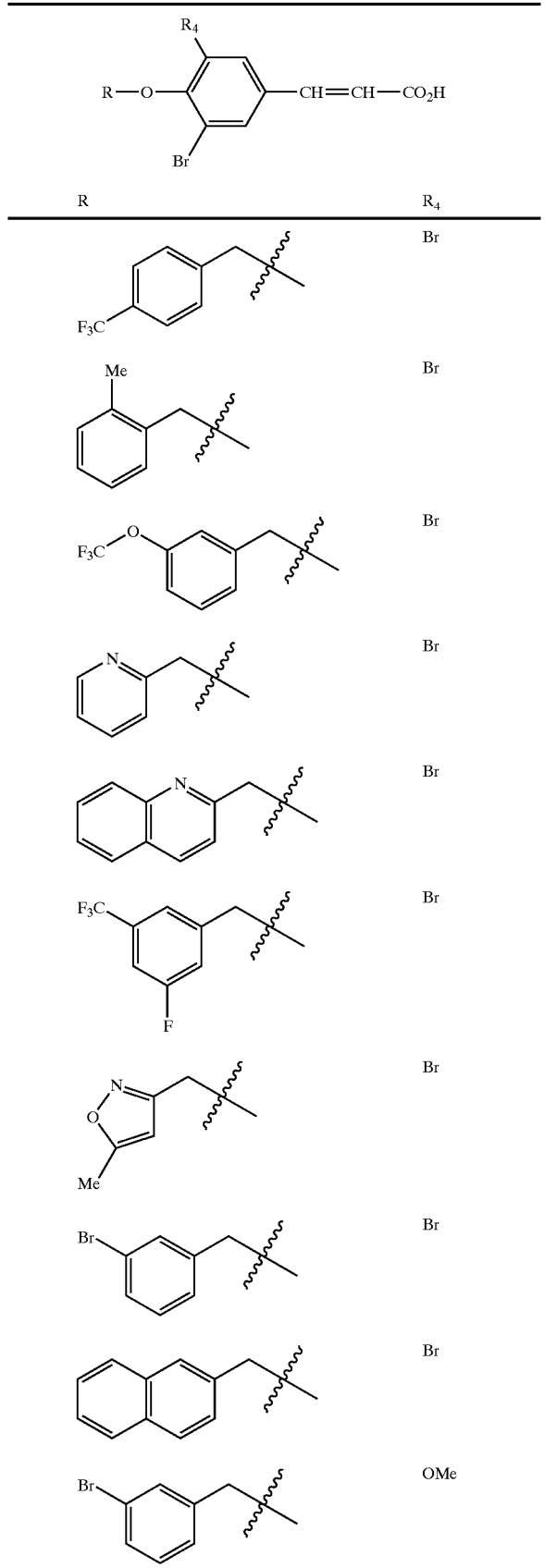

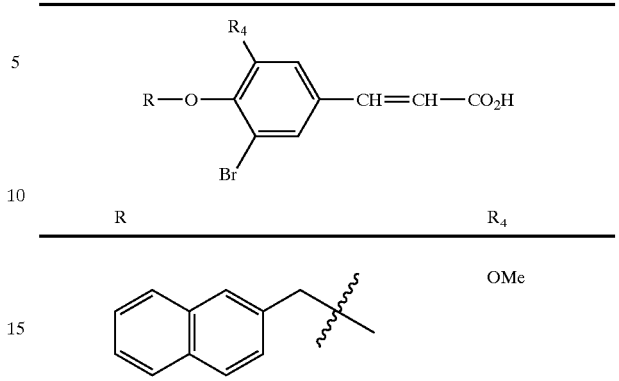

or pharmaceutically acceptable salts thereof and stereoisomers thereof.

The compounds of the invention are antagonists or partial antagonists, preferably α-selective. As such they are useful in medical therapy. Furthermore, they are useful in the prevention, inhibition or treatment of a disease which is dependent on the expression of a $T_3$ regulated gene or associated with metabolic dysfunction. Examples of such diseases are heart related disorders, such as cardiac arrhytmias (atrial and ventricular arrhythmias), especially atrial fibrillation and ventricular tachycardia and fibrillation. The compounds of the invention may also be useful for the treatment of thyrotoxicosis, especially in the therapy of elderly patients, subclinical hyperthyroidism, and other related endocrine disorders, related to thyroid hormone.

The compounds of the invention may also be used to treat certain skin disorders or diseases such as keloids, roughened skin, lichen planus, ichtyosis, acne, psoriasis, Demier's disease, eczema, chloracne, atopic dermatitis, pityriasis, hirsuitism and skin scarring. In treating skin disorders or diseases as described above, the compounds of the invention may be used in combination with a retinoid or a vitamin D analog.

Exemplifying the invention is a pharmaceutical composition comprising any of the compounds described above and a pharmaceutically acceptable carrier. Also exemplifying the invention is a pharmaceutical composition made by combining any of the compounds described above and a pharmaceutically acceptable carrier. An illustration of the invention is a process for making a pharmaceutical composition comprising combining any of the compounds described above and a pharmaceutically acceptable carrier.

Another embodiment of the invention is a method of treating, inhibiting or preventing a disease which is dependent on the expression of a $T_3$ regulated gene or associated with metabolic dysfunction in a mammal in need thereof by administering to the mammal a therapeutically effective amount of any of the compounds or pharmaceutical compositions described above. The said diseases may be heart related disorders, such as cardiac arrhytmias (atrial and ventricular arrhythmias), especially atrial fibrillation and ventricular tachycardia and fibrillation, especially in the therapy of elderly patients, subclinical hyperthyroidism, and other related endocrine disorders, related to thyroid hormone.

Yet another embodiment of the invention is a method of treating, inhibiting or preventing certain skin disorders or diseases such as keloids, roughened skin, lichen planus, ichtyosis, acne, psoriasis, Dernier's disease, eczema, chloracne, atopic dermatitis, pityriasis, hirsuitism and skin scarring. In treating skin disorders or diseases as described above, the compounds of the invention may be used in combination with a retinoid or a vitamin D analog.

Further exemplifying the invention is the use of any of the compounds described above in the preparation of a medicament for the treatment, inhibition or prevention of a disease which is dependent on the expression of a $T_3$ regulated gene or associated with metabolic dysfunction. Still further exemplifying the invention is the use of any of the compounds desribed above in the preparation of a medicament for the treatment and/or prevention of heart related disorders, such as cardiac arrhytmias (atrial and ventricular arrhythmias), especially atrial fibrillation and ventricular tachycardia and fibrillation, especially in the therapy of elderly patients, subclinical hyperthyroidism, and other related endocrine disorders, related to thyroid hormone.

Further exemplifying the invention is the use of any of the compounds described above in the preparation of a medicament for the treatment, inhibition or prevention of certain skin disorders or diseases such as keloids, roughened skin, lichen planus, ichtyosis, acne, psoriasis, Dernier's disease, eczema, chloracne, atopic dermatitis, pityriasis, hirsuitism and skin scarring. In treating skin disorders or diseases as described above, the compounds of the invention may be used in combination with a retinoid or a vitamin D analog.

The compounds of the present invention can be administered in such oral dosage forms as tablets, capsules (each of which includes sustained release or timed release formulations), pills, powder, granules, elixirs, tinctures, suspensions, syrups and emulsions. Likewise, they may also be administered in intravenous (bolus or infusion), intraperitoneal, topical (e.g., ocular eyedrop), subcutaneous, intramuscular, or transdermal (e.g., patch) form, all using forms well known to those of ordinary skill in the pharmaceutical arts.

The dosage regimen utilizing the compounds of the present invention is selected in accordance with a variety of factors including type, species, age, weight, sex, and medical condition of the patient; the severity of the condition to be treated; the route of administration; the renal and hepatic function of the patient; and the particular compound or salt thereof employed. An ordinarily skilled physician, veterinarian or clinician can readily determine and prescribe the effective amount of the drug required to prevent, counter or arrest the progress of the condition.

Oral dosages of the present invention, when used for the indicated effects, will range between about 0.01 mg per kg of body weight per day (mg/kg/day) to about 100 mg/kg/day, preferably 0.01 mg per kg of body weight per day (mg/kg/day) to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100, and 500 milligrams of the active ingredient for the symptomatic adjustment of the dosage to the patient to be treated. A medicament typically contains from about 0.01 mg to about 500 mg of the active ingredient, preferably from about 1 mg to about 100 mg of active ingredient. Intravenously, the most preferred doses will range from about 0.1 to about 10 mg/kg/minute during a constant rate infusion. Advantageously, compounds of the present invention may be admin istered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches will known to those of ordinary skill in the art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, exipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms includes sodium oleate, sodium stearate, magnesium stearate, sodium benzoate, sodium acetate, sodium chloride and the like. Disintegrators include without limitation starch, methylcellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed form a variety of phospholipids, such as cholesterol, stearylamine or phosphatidylcholines.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example in "Design of Prodrugs" ed. H. Bundgaard, Elsevier, 1985, which is incorporated by reference herein in its entirety. Metabolites of the compounds includes active species produced upon introduction of compounds of this invention into the biological milieu.

The following Examples represent preferred embodiments of the present invention. However, they should not be construed as limiting the invention in any way. The $^1$H NMR spectra was all consistent with the assigned structures in the Examples.

General Procedure for the Preparation of Examples 1–13 (Method A).

A mixture of the appropriate phenol (1.5 mmol) and potassium carbonate (0.85 g, 6.2 mmol) in acetone (3 mL) was stirred at room temperature. After 10 minutes the bromo compound (6.2 mmol) was added. The reaction mixture was heated at reflux over night, cooled to room temperature and concentrated in vacuo. Diethyl ether was added to the residue, the solution filtered on silica gel and the resulting filtrate concentrated. The residue was dissolved in 12 mL of methanol. An aqueous solution of sodium hydroxide (8 mL, 1 N) was added dropwise and the reaction mixture was stirred at room temperature for 16 hours, and acidified with hydrochloric acid (1N). The precipitate formed was collected and dried.

General Procedure for the Preparation of Examples 14–20 (Method B).

A solution of the phenol (0.1 mmol), triethylamine (0.4 mmol) and acetone (0.5 mL) was stirred under nitrogen for 30 minutes. This solution was added to the appropriate bromide (0.4 mmol) in acetone (0.3 mL), the vessel sealed under nitrogen, and heated at 60° C. over night. After cooling to room temperature, the reaction mixture was concentrated in vacuo. The residue was suspended in sodium hydroxide (1N, 1 mL), the vessel sealed and stirred at room temperature. After 24 hours, hydrochloric acid (6 N, 0.5 mL) was added followed by ethyl acetate (2 mL). The mixture was shaken and placed on a separate ChemElute cartridge. After 5 minutes the cartridge was washed successively with ethyl acetate (3×1 mL), the precipiate collected and dried.

General Procedure for the Preparation of Examples 21–30 (Method C).

A mixture of the appropriate phenol (0.36 mmol) and potassium carbonate (0.2 g, 1.45 mmol) in 6 mL of acetone was stirred at room temperature. After 10 minutes the bromo compound (1.4 mmol) was added. The reaction mixture was heated under reflux over night, cooled to room temperature and concentrated in vacuo. Diethyl ether was added to the residue and filtered through a celite pad. The resulting filtrate was concentrated and the residue was dissolved in methanol (10 mL). An aqueous solution of sodium hydroxide (2 mL, 1N) was added dropwise and the reaction mixture was stirred over night at room temperature. The solution was acidified with hydrochloric acid (2 N) and the volatiles were removed in vacuo. The precipitate was collected, washed with water and purified by column chromatography (silica gel, gradient of chloroform and chloroform/methanol (from 90–10%).

For a table of Examples 1–30 comprising the Examples, methods, yields and mass spectras, see Scheme below.

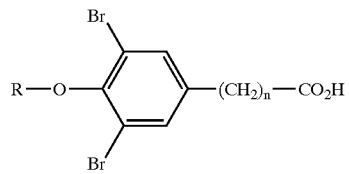

| Example | R | n | Method | Yield[1] | MS[2] |
|---|---|---|---|---|---|
| 1 | *sec-butyl* | 1 | A | 89 | 365.2 |
| 2 | *isobutyl* | 1 | A | 32 | 365.2 |
| 3 | *n-pentyl* | 1 | A | 81 | 379 |
| 4 | *isopentyl* | 1 | A | 90 | 379 |
| 5 | *n-hexyl* | 1 | A | 71 | 393.1 |
| 6 | *2-ethylbutyl* | 1 | A | 79 | 393.1 |
| 7 | *cyclohexylmethyl* | 1 | A | 74 | 405.1 |
| 8 | *sec-butyl* | 2 | A | 68 | 379 |
| 9 | *n-butyl* | 2 | A | 88 | 293.1 |
| 10 | *n-hexyl* | 2 | A | 92 | 407.2 |
| 11 | *isohexyl* | 2 | A | 90 | 393.1 |

-continued

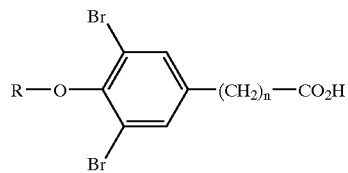

| Example | R | n | Method | Yield[1] | MS[2] |
|---|---|---|---|---|---|
| 12 | 3-pentyl | 2 | A | 70[3] | 407.2 |
| 13 | cyclohexylmethyl | 2 | A | 63 | 419.2 |
| 14 | 3-cyclohexylpropyl | 2 | B | 30 | — |
| 15 | 3-methylbenzyl | 2 | B | 66 | 428.1 |
| 16 | cis-2-pentenyl | 2 | B | 64 | 391 |
| 17 | benzyl | 2 | B | 82 | 412.9 |
| 18 | 4-pentenyl | 2 | B | 77 | 390.4 |
| 19 | 2-pentynyl | 2 | B | 50 | — |
| 20 | pentyl | 1 | A | 96 | 365.2 |
| 21 | 2,5-cyclohexadienylmethyl | 1 | C | 37 | 400.1 |

-continued

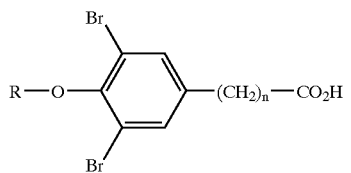

| Example | R | n | Method | Yield[1] | MS[2] |
|---|---|---|---|---|---|
| 22 | 3-(trifluoromethyl)benzyl | 2 | C | 84 | 482.1 |
| 23 | 3-bromobenzyl | 2 | C | 67 | 493 |
| 24 | 2-methylbenzyl | 2 | C | 97 | 428.1 |
| 25 | 4-methylbenzyl | 2 | C | 95 | 428.1 |
| 26 | 3,5-dimethylbenzyl | 2 | C | 75 | 442.1 |
| 27 | 4-fluorobenzyl | 2 | C[4] | 5 | 432.1 |
| 28 | 4-(trifluoromethyl)benzyl | 2 | C[4] | 42 | 482.1 |
| 29 | 3-nitrobenzyl | 2 | C | 65 | 459.1 |

-continued

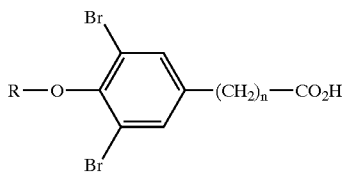

| Example | R | n | Method | Yield[1] | MS[2] |
|---|---|---|---|---|---|
| 30 | 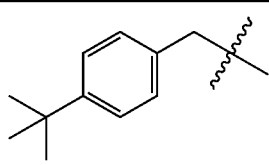 | 2 | C[4] | 4 | 470.2 |

[1]Yields in %.
[2]MS result obtained on a Perkin-Elmer API 150Ex spectrometer, using electrospray negative ion mode.
[3]This substance fell as an oil during final work-up. In order to get crystals the methanol was removed in vacuo and the remaining water phase, extracted with ethyl acetate. After drying over magnesium sulphate and removal of the organic phase, a crystal mass was obtained.
[4]In Examples 27, 28 and 30, the final compound was first separated in 2 g silica pre-packed in 3 mL SPE cartridges employing the same gradient of solvents described in Procedure C and then further purified by semi-preparative-HPLC (Zorbax CombiHT (SB-C8 50 × 21.2 mm, 5µ) Mobil Phase: Solvent A. Water with 0.5% formic acid; Solvent B: acetonitrile. Gradient: 2 min 80% of A then over 8 min to 5% of A).

Example 31

N-[3,5-Dibromo-4-(3-bromobenzyloxy)benzoyl]benzenesulphonamide

To a stirred mixture of benzenesulphonamide (0.89 mmol), dichloromethane (1 mL) and dimethylformamide (one drop), a solution of 3,5-dibromo-4-(3-bromo-benzyloxy)benzoic acid (0.17 mmol) and N,N-diisopropylethylamine (0.86 mmol) in dichloromethane (1 mL) was added. After 15 minutes bromotripyrrolidino phosphoniumhexafluoro phosphate (0.21 mmol) and 1-hydroxybenzotriazole hydrate (0.045 mmol) were added. The reaction mixture was stirred at room temperature over night. Dichloromethane was added (3 mL) and the mixture was washed with an aqueous solution of citric acid (10%, 3×3 mL). The organic layer was washed with brine, dried over magnesium sulphate and concentrated in vacuo. The residue was purified on column (silica gel, chloroform/methanol 19:1) and further purified on semi-preparative HPLC (column and eluents as described for Examples 27, 28 an 30) to give 16 mg (16%) of N-[3,5-dibromo-4-(3-bromobenzyloxy)benzoyl]benzenesulphonamide.

Example 32

N-[3,5-Dibromo-4-(3-bromobenzyloxy)benzoyl]-3-nitrobenzenesulphonamide 3,5-dibromo-4-(3-bromobenzyloxy)benzoic acid (0.17 mmol) was coupled with 3-nitrobenzenesulphonamide (0.89 mmol) using the procedure described in Example 31. Purification on column (silica gel, chloroform/methanol 9:1) gave 60 mg (54%) of N-[3,5-dibromo-4-(3-bromobenzyloxy)benzoyl]-3-nitrobenzenesulphonamide.

Example 33

N-[3,5-Dibromo-4-(3-bromobenzyloxy)benzoyl]-4-nitrobenzenesulphonamide 3,5-Dibromo-4-(3-bromobenzyloxy)benzoic acid (0.13 mmol) was coupled with 4-nitrobenzenesulphonamide (0.64 mmol) using the procedure described in Example 31. Purification on column (silica gel, chloroform/methanol 9:1) gave 58 mg (69%) of N-[3,5-dibromo-4-(3-bromobenzyloxy)benzoyl]-4-nitrobenzene-sulphonamide.

Example 34

4-Amino-N-[3,5-dibromo-4-(3-bromobenzyloxy)benzoyl]benzenesulphonamide

To a solution of N-[3,5-dibromo-4-(3-bromobenzyloxy)benzoyl]-4-nitrobenzenesulphonamide (0.25 mmol), prepared as described in Example 33, in ethanol (95%, 25 mL), sodium dithionite (1.26 mmol) was added and the reaction mixture stirred over night at 70° C. The reaction mixture was allowed to reach room temperature and then evaporated in vacuo. The residue was diluted with ethyl acetate and washed with an aqueous solution of sodium hydrogencarbonate (saturated). The organic phase was dried over magnesium sulphate and concentrated in vacuo. The residue was purified on column (silica gel, chloroform/methanol 17:3) and further purified by semi-preparative HPLC (column and eluents as described for Examples 27, 28 an 30) to give 30 mg (20%) of 4-amino-N-[3,5-dibromo-4-(3-bromobenzyloxy)-benzoyl]benzenesulphonamide.

Example 35

N-[3,5-Dibromo-4-(3-bromobenzyloxy)benzoyl]methanesulphonamide 3,5-Dibromo-4-(3-bromobenzyloxy)benzoic acid (0.15 mmol) was coupled with methanesulphonamide (0.77 mmol) using the procedure described in Example 31. Purification on column (silica gel, chloroform/methanol 9:1) gave 55 mg (67%) of N-[3,5-dibromo-4-(3-bromobenzyloxy)benzoyl]methanesulphonamide.

General Procedure for the Preparation of Examples 36–100 (Method D1, D2, D3 and D4)

To a solution of the appropriate phenol (0.035 mmol) in acetone or dry acetonitrile (0.25 mL) was added potassium carbonate (0.070 or 0.14 mmol) and the resulting mixture was stirred at room temperature. After 10 minutes a solution of the halide (0.070 or 0.14 mmol) in acetone or acetonitrile (0.25 mL) was added. When the halide was a chloride, a catalytic amount of sodium iodide was added. The mixture was heated at 60° C. (acetone) or 80° C. (acetonitrile) over night. After cooling down to room temperature, the reaction mixture was filtered through a silica SPE column (500 mg/3 mL), eluting with n-heptane/ethyl acetate 3:1 (3 mL). After concentration in vacuo the residue was hydrolysed according to method D1, D2, D3 or D4.

Method D1: The residue was dissolved in methanol (0.25 mL), sodium hydroxide (1 N in water, 0.25 mL) was added and the mixture was stirred at room temperature over night. After acidification with hydrochloric acid (1 N) the product was extracted into ethyl acetate.

Method D2: The residue was dissolved in dry dichloromethane (0.5 mL) and potassium trimethylsilanolate (9 mg, 0.070 mmol, 2 equiv) was added. The reaction mixture was stirred at room temperature over night. After concentration, the residue was dissolved in methanol and neutralised on an SCX SPE column, using methanol as eluent.

Method D3: The residue was dissolved in dry tetrahydrofuran (0.5 mL) and potassium trimethylsilanolate (9 mg, 0.070 mmol, 2 equiv) was added. The reaction mixture was stirred at room temperature until TLC showed complete consumption of the starting material (0.5-2 h). The mixture was neutralised on an SCX SPE column, using methanol as eluent.

Method D4: The residue was dissolved in tetrahydrofuran (0.25 mL) and lithium hydroxide (1 N in water, 0.25 mL) was added. The reaction mixture was stirred at room temperature. After 4 hours the mixture was neutralised on an SCX SPE column (500 mg/3 mL), using methanol or triethylamine (10% in methanol) as eluent.

Methods D1–D4: The solvent was concentrated and the residue purified on a silica SPE column (500 mg/3 mL, heptane/ethyl acetate 9:1 (3 mL) followed by dichloromethane/methanol 9:1 (3 mL)). The product containing fractions were collected and concentrated in vacuo to give the final product.

For a table of Examples 36–100 comprising the Examples, used solvents, hydrolysis method, yields and mass spectras, see Scheme below.

| Example | R | $R_3, R_4$ | Y | n | Solvent | Equiv. halide | Hydrol. Method | Yield (%) | MS[1] |
|---|---|---|---|---|---|---|---|---|---|
| 36 | 2-ethylhexyl | Br | $CH_2$ | 0 | acetone | 4 | D1 | 27 | 421.0 |
| 37 | cyclopropylmethyl | Br | $CH_2$ | 0 | acetone | 4 | D4 | 75 | 363.1 |
| 38 | 2-naphthylmethyl | Br | $CH_2$ | 1 | acetone | 4 | D2 | 34 | 463.0 |
| 39 | 3,5-dibromobenzyl | Br | $CH_2$ | 1 | $CH_3CN$ | 2 | D3 | 38 | 570.7 |
| 40 | 3-cyanobenzyl | Br | $CH_2$ | 1 | $CH_3CN$ | 2 | D3 | 51 | 437.8 |
| 41 | 3-methoxybenzyl | Br | $CH_2$ | 1 | $CH_3CN$ | 2 | D3 | 91 | 443.2 |
| 42 | pentyl | Cl | CHOH | 0 | $CH_3CN$ | 2 | D4 | 58 | 290.8 |
| 43 | heptyl | Cl | CHOH | 0 | $CH_3CN$ | 2 | D4 | 52 | 333.1 |

-continued

| Example | R | R₃, R₄ | Y | n | Solvent | Equiv. halide | Hydrol. Method | Yield (%) | MS[1] |
|---|---|---|---|---|---|---|---|---|---|
| 44 | 3-Br-benzyl | Cl | CHOH | 0 | $CH_3CN$ | 2 | D4 | 64 | 404.8 |
| 45 | n-butyl | Cl | C=O | 0 | $CH_3CN$ | 2 | D4 | 48 | 289.0 |
| 46 | n-octyl | Cl | C=O | 0 | $CH_3CN$ | 2 | D4 | 12 | 330.7 |
| 47 | 3-Br-benzyl | Cl | C=O | 0 | $CH_3CN$ | 2 | D4 | 64 | 402.7 |
| 48 | 3,5-diMe-benzyl | Cl | C=O | 0 | $CH_3CN$ | 2 | D4 | 7 | 351.1 |
| 49 | 3-OMe-benzyl | Cl | C=O | 0 | $CH_3CN$ | 2 | D4 | 63 | 352.9 |
| 50 | n-butyl | Me | $CH_2$ | 0 | $CH_3CN$ | 2 | D4 | 61 | 235.0 |
| 51 | cyclohexylmethyl | Me | $CH_2$ | 0 | $CH_3CN$ | 2 | D4 | 46 | 275.2 |
| 52 | n-heptyl | Me | $CH_2$ | 0 | $CH_3CN$ | 2 | D4 | 61 | 277.0 |
| 53 | 3-Br-benzyl | Me | $CH_2$ | 0 | $CH_3CN$ | 2 | D4 | 78 | 349.0 |

-continued
| Example | R | $R_3, R_4$ | Y | n | Solvent | Equiv. halide | Hydrol. Method | Yield (%) | MS[1] |
|---|---|---|---|---|---|---|---|---|---|
| 54 | 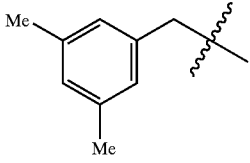 | Me | $CH_2$ | 0 | $CH_3CN$ | 2 | D4 | 76 | 297.1 |
| 55 | 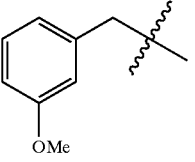 | Me | $CH_2$ | 0 | $CH_3CN$ | 2 | D4 | 85 | 299.2 |
| 56 | 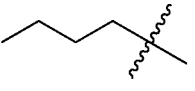 | Me | C=O | 0 | $CH_3CN$ | 2 | D4 | 43 | 248.8 |
| 57 | 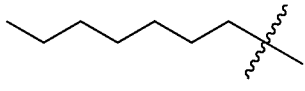 | Me | C=O | 0 | $CH_3CN$ | 2 | D4 | 82 | 290.8 |
| 58 | 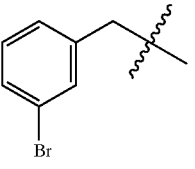 | Me | C=O | 0 | $CH_3CN$ | 2 | D4 | 93 | 361.0 |
| 59 | 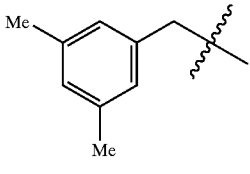 | Me | C=O | 0 | $CH_3CN$ | 2 | D4 | 85 | 310.9 |
| 60 | 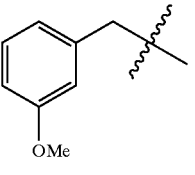 | Me | C=O | 0 | $CH_3CN$ | 2 | D4 | 86 | 313.0 |
| 61 | 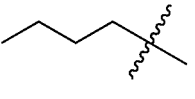 | i-Pr | C=O | 0 | $CH_3CN$ | 2 | D4 | 55 | 305.2 |
| 62 | 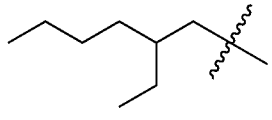 | i-Pr | C=O | 0 | acetone | 4 | D1 | 26 | 361.3 |
| 63 | 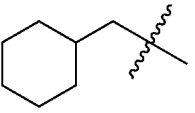 | i-Pr | C=O | 0 | $CH_3CN$ | 2 | D4 | 53 | 344.8 |
| 64 | 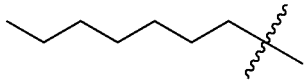 | i-Pr | C=O | 0 | $CH_3CN$ | 2 | D4 | 51 | 346.9 |

-continued

| Example | R | R₃, R₄ | Y | n | Solvent | Equiv. halide | Hydrol. Method | Yield (%) | MS[1] |
|---|---|---|---|---|---|---|---|---|---|
| 65 | 3-Br-phenyl-CH< | i-Pr | C=O | 0 | $CH_3CN$ | 2 | D4 | 61 | 417.1 |
| 66 | 3,5-diMe-phenyl-CH< | i-Pr | C=O | 0 | $CH_3CN$ | 2 | D4 | 72 | 367.0 |
| 67 | 3-OMe-phenyl-CH< | i-Pr | C=O | 0 | $CH_3CN$ | 2 | D4 | 72 | 368.8 |
| 68 | n-butyl-CH< | i-Pr | $CH_2$ | 0 | $CH_3CN$ | 2 | D4 | 41 | 291.1 |
| 69 | 3-Br-phenyl-CH< | i-Pr | $CH_2$ | 0 | $CH_3CN$ | 2 | D4 | 25 | 405.1 |
| 70 | 3,5-diMe-phenyl-CH< | i-Pr | $CH_2$ | 0 | $CH_3CN$ | 2 | D4 | 23 | 353.2 |
| 71 | 3-OMe-phenyl-CH< | i-Pr | $CH_2$ | 0 | $CH_3CN$ | 2 | D4 | 25 | 355.0 |
| 72 | 3-OCF₃-phenyl-CH< | Br | $CH_2$ | 1 | $CH_3CN$ | 2 | D4 | 100 | 497.2 |
| 73 | 3-CF₃-5-F-phenyl-CH< | Br | $CH_2$ | 1 | $CH_3CN$ | 2 | D4 | 86 | 499 |

-continued

| Example | R | $R_3, R_4$ | Y | n | Solvent | Equiv. halide | Hydrol. Method | Yield (%) | MS[1] |
|---|---|---|---|---|---|---|---|---|---|
| 74 | 3-F-phenyl-CH₂- | Br | CH₂ | 1 | CH₃CN | 2 | D4 | 100 | 430.9 |
| 75 | 3,5-diF-phenyl-CH₂- | Br | CH₂ | 1 | CH₃CN | 2 | D4 | 100 | 448.9 |
| 76 | 3,5-bis(CF₃)-phenyl-CH₂- | Br | CH₂ | 1 | CH₃CN | 2 | D4 | 61 | 549.1 |
| 77 | 3-(F₂HCO)-phenyl-CH₂- | Br | CH₂ | 1 | CH₃CN | 2 | D4 | 91 | 478.9 |
| 78 | naphthalen-1-yl-CH₂- | Br | CH₂ | 1 | CH₃CN | 2 | D4 | 100 | 463.0 |
| 79 | pyridin-2-yl-CH₂- | Br | CH₂ | 1 | CH₃CN | 2 | D4 | 49 | 413.8 |
| 80 | pyridin-3-yl-CH₂- | Br | CH₂ | 1 | CH₃CN | 2 | D4 | 32 | 413.8 |
| 81 | pyridin-4-yl-CH₂- | Br | CH₂ | 1 | CH₃CN | 2 | D4 | 58 | 413.8 |
| 82 | quinolin-2-yl-CH₂- | Br | CH₂ | 1 | CH₃CN | 2 | D4 | 93 | 463.9 |
| 83 | 4-Cl-benzo[b]thiophen-3-yl-CH₂- | Br | CH₂ | 1 | CH₃CN | 2 | D4 | 9 | 502.9 |

-continued
| Example | R | R₃, R₄ | Y | n | Solvent | Equiv. halide | Hydrol. Method | Yield (%) | MS[1] |
|---|---|---|---|---|---|---|---|---|---|
| 84 | 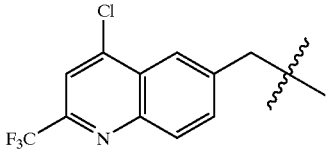 | Br | CH₂ | 1 | CH₃CN | 2 | D4 | 63 | 565.9 |
| 85 | 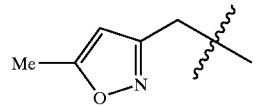 | Br | CH₂ | 1 | CH₃CN | 2 | D4 | 88 | 418.0 |
| 86 | 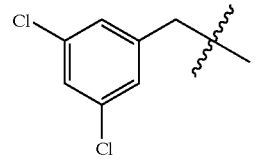 | Br | CH₂ | 1 | CH₃CN | 2 | D4 | 46 | 480.7 |
| 87 | 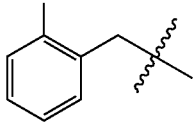 | Br | CH₂ | 1 | CH₃CN | 2 | D4 | 38 | 430.9 |
| 88 | 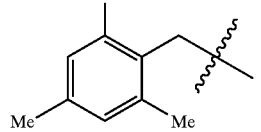 | Br | CH₂ | 1 | CH₃CN | 2 | D4 | 76 | 454.9 |
| 89 | 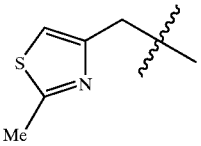 | Br | CH₂ | 1 | CH₃CN | 2 | D4 | 46 | 433.9 |
| 90 | 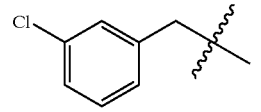 | Br | CH₂ | 1 | CH₃CN | 2 | D4 | 94 | 446.8 |
| 91 | 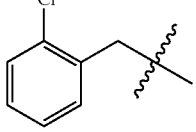 | Br | CH₂ | 1 | CH₃CN | 2 | D4 | 97 | 446.8 |
| 92 | 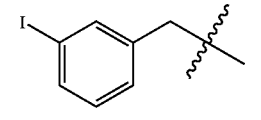 | Br | CH₂ | 1 | CH₃CN | 2 | D4 | 30 | 538.9 |
| 93 | 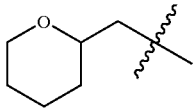 | Br | CH₂ | 1 | CH₃CN | 2 | D4 | 76 | 421.0 |

-continued

| Example | R | $R_3, R_4$ | Y | n | Solvent | Equiv. halide | Hydrol. Method | Yield (%) | MS[1] |
|---|---|---|---|---|---|---|---|---|---|
| 94 | 2-NO₂-phenyl-CH₂- | Br | CH₂ | 1 | CH₃CN | 2 | D4 | 36 | 457.9 |
| 95 | 2-(OCHF₂)-phenyl-CH₂- | Br | CH₂ | 1 | CH₃CN | 2 | D4 | 17 | 478.9 |
| 96 | 2-(OCF₃)-phenyl-CH₂- | Br | CH₂ | 1 | CH₃CN | 2 | D4 | 28 | 497.2 |
| 97 | 1-Br-6-F-naphthyl-2-CH₂- | Br | CH₂ | 1 | CH₃CN | 2 | D4 | 29 | 559.0 |
| 98 | 2-CF₃-phenyl-CH₂- | Br | CH₂ | 1 | CH₃CN | 2 | D4 | 20 | 481.0 |
| 99 | 1-Br-naphthyl-2-CH₂- | Br | CH₂ | 1 | CH₃CN | 2 | D4 | 25 | 541.0 |
| 100 | 6-MeO-naphthyl-2-CH₂- | Br | CH₂ | 1 | CH₃CN | 2 | D4 | 41 | 493.0 |

[1]MS result obtained on a Perkin-Elmer API 150Ex spectrometer, using electrospray negative ion mode.

Example 101

3-[3,5-Dibromo-4-(3-ethoxybenzyloxy)phenyl]propionic Acid (a) Methyl 3-(3,5-dibromo-4-hydroxyphenyl)propionate (0.15 g, 0.44 mmol) was coupled with 3-bromomethylphenyl acetate (0.20 g, 0.88 mmol) using the procedure described in Method D4. Purification on column (silica gel, dichloromethane/methanol, gradient elution from 95:5 to 90:10) gave 123 mg (78%) of 3-[3,5-dibromo-4-(3-hydroxybenzyloxy)phenyl]propionic acid. MS: m/z 430.1 ($M^+-1$).

(b) 3,5-dibromo-4-(3-hydroxybenzyloxy)phenyl]propionic acid was coupled with ethylbromide (4 equivalents) in acetonitrile, using the procedure described in Method D4, to give 9 mg (56%) of 3,5-dibromo-4-(3-ethoxybenzyloxy)phenyl]propionic acid. MS: m/z 457.0 ($M^+-1$).

Example 102

3-[3,5-Dibromo-4(3-propyloxybenzyloxy)phenyl]propionic Acid

3-[3,5-Dibromo-4-(3-hydroxybenzyloxy)phenyl]propionic acid was coupled with propylbromide using the procedure described in Example 101(b), to give 8 mg (50%) of 3,5-dibromo-4-(3-propyloxybenzyloxy)phenyl]propionic acid. MS: m/z 471.1 ($M^+-1$).

Example 103

3-[3,5-Dibromo-4-(3-butyloxybenzyloxy)phenyl]propionic Acid 3,5-dibromo-4-(3-hydroxybenzyloxy)phenyl]propionic acid was coupled with butylbromide using the procedure described in Example 101(b), to give 8 mg (50%) of 3,5-dibromo-4-(3-butyloxybenzyloxy)phenyl]propionic acid. MS: m/z 484.9 ($M^+-1$)

Example 104

3-[3,5-Dibromo-4-(3-aminobenzyloxy)phenyl]propionic Acid

A mixture of 3-[3,5-dibromo-4-(3-nitrobenzyloxy)phenyl]propionic acid (0.66 g, 1.44 mmol) and $Na_2S_2O_4$ (2.0 g, 11.5 mmol) in ethanol (50 mL, 90%) was stirred at 70° C. over night. The reaction mixture was concentrated and purified on column (silica gel, chloroform/methanol, 9:1), to give 0.18 g (29%) of 3-[3,5-dibromo-4-(3-amino-benzyloxy)phenyl]propionic acid. MS: m/z 429.1 ($M^+-1$).

Example 105

3-[3,5-Dibromo-4-(3-ethylaminebenzyloxy)phenyl]propionic Acid

Sodium boron hydride (6.6 mg, 0.17 mmol) was added in portions to a stirred solution of 3-[3,5-dibromo-4-(3-aminobenzyloxy)phenyl]propionic acid (15 mg, 0.035 mmol) in glacial acetic acid (2 mL) at room temperature. After 5.5 hours the reaction was quenched with water, extracted with diethyl ether and purified on semi-preperative HPLC using the same conditions as described for Examples 27, 28 and 30. This gave 4.0 mg (25%) of 3-[3,5-dibromo-4-(3-ethylaminebenzyloxy)-phenyl]propionic acid. MS: m/z 457.2 ($M^+-1$).

Example 106

3-[3,5-Dibromo-4-(3-diethylaminebenzyloxy)phenyl]propionic Acid

Sodium boron hydride (17.6 mg, 0.47 mmol) was added in portions to a stirred solution of 3-[3,5-dibromo-4-(3-aminobenzyloxy)phenyl]propionic acid (40 mg, 0.090 mmol) in glacial acetic acid (5 mL) at room temperature. The reaction mixture was heated at 55 C for 2.5 hours. The reaction was cooled down to room temperature, quenched and purified on semi-preperative HPLC using the same conditions as described for Examples 27, 28 and 30. This gave 19 mg (42%) of 3-[3,5-dibromo-4-(3-diethylaminebenzyloxy)phenyl]propionic acid. MS: m/z 485.2 ($M^+-1$).

Example 107

N-[3,5-Dibromo-4-(3-bromobenzyloxy)phenyl]oxamic Acid (a) 3,5-Dibromo-4-hydroxynitrobenzene (40 mg, 0.13 mmol) was coupled with benzylbromide (0.26 mmol) using the procedure described in Method C. The crude material was used directly in the next step without additional purification on column. The crude material was dissolved in ethanol (3 mL) and treated with sodium dithionite (0.19 g, 1,1 mmol). After heating at 70° C. over night, the reaction mixture was concentrated and dissolved in ethyl acetate. The organic phase was washed with an aqueous hydrochloric acid (0.01N), water and dried over $MgSO_4$. After concentration of the organic phase, the residue was treated with diethyl oxalate (0.5 mL). The reaction mixture was heated at 100 C for one hour and then at 180° C. for 10 minutes. After cooling down to room temperature, the reaction mixture was purified on semi-preperative HPLC using the same conditions as described for Examples 27, 28 and 30. This gave 19 mg (26%) of ethyl-N-[3,5-dibromo-4-(3-bromobenzyloxy)-phenyl]oxamate. MS: m/z 536.0 ($M^+-1$).

(b) Ethyl-N-[3,5-dibromo-4-(3-bromobenzyloxy)phenyl] oxamate (18 mg) was dissolved in methanol (1 mL) and treated with sodium hydroxide (IN, 6–8 equivalents). After stirring over night at room temperature, the reaction mixture was acidified to pH 5. The mixture was purified on semi-preperative HPLC using the same conditions as described for Examples 27, 28 and 30. This gave 7.8 mg (46%) of N-[3,5-dibromo-4-(3-bromobenzyloxy)phenyl]oxamic acid. MS: m/z 508.0 ($M^+-1$).

Example 108

N-[3,5-Dibromo-4-(2-methylnaphthyloxy)phenyl] oxamic Acid 3,5-Dibromo-4-hydroxynitrobenzene (40 mg, 0.13 mmol) was coupled with 2-(bromomethyl)naphthalene (0.26 mmol), reduced with sodium dithionite, coupled with diethyloxalate and hydrolyzed in a similar manner as described in Example 107. This gave 26% N-[3,5-dibromo-4-(2-methylnaphthyloxy)phenyl]oxamic acid. MS: m/z 479.1 ($M^+-1$).

Example 109

3-[3-bromo-5-methoxy-4(3-bromobenzyloxy)phenyl]propionic Acid

Methyl 3-(3-bromo-4-hydroxy-5-methoxyphenyl) propionate (0.14 mmol) was coupled with benzylbromide (0.28 mmol) and hydrolyzed, using the procedure described for Examples 21–30 (Method C). This gave 15% yield of 3-[3-bromo-5-methoxy-4-(3-bromobenzyloxy)phenyl]propionic acid. MS: m/z 444.1 ($M^+$–1).

Example 110

3-[3-bromo-5-methoxy-4-(2-methylnaphthyloxy)phenyl]propionic Acid

Methyl-3-(3-bromo-4-hydroxy-5-methoxyphenyl) propionate (0.14 mmol) was coupled with 2-(bromomethyl)naphthalene (0.28 mmol) and hydrolyzed, using the procedure described for Examples 21–30 (Method C). This gave 18% yield of 3-[3-bromo-5-methoxy-4-(2-methylnaphthyloxy)phenyl]propionic acid. MS: m/z 415.3 ($M^+$–1).

General Procedure for the Preparation of Examples 111–119

To a solution of methyl 3-(3,5-dibromo-4-hydroxyphenyl) cinnamate (0.035 mmol) (prepared according to Schreiber, F. G; Stevenson, R., J. *Chem. Soc., Perkin Trans.* 1, 1976, 14, 1514–18 and references cited therein) in dry acetonitrile (0.25 mL) was added potassium carbonate (0.070 mmol) and the resulting mixture was stirred at room temperature. After 10 minutes a solution of the halide (0.070 mmol) in acetonitrile (0.25 mL) was added. When the halide was a chloride, a catalytic amount of sodium iodide was added. The mixture was heated at 80° C. over night. After cooling down to room temperature, the reaction mixture was filtered through a silica SPE column (500 mg/3 mL), eluting with n-heptane/ethyl acetate 3:1 (3 mL). After concentration in vacuo the residue was dissolved in tetrahydrofuran (0.25 mL) and lithium hydroxide (1 N in water, 0.25 mL) was added. The reaction mixture was stirred at room temperature. After 4 hours the mixture was neutralised on an SCX SPE column (500 mg/3 mL), using methanol or triethylamine (10% in methanol) as eluent. The eluent was concentrated and the residue purified on a silica SPE column (500 mg/3 mL, heptane/ethyl acetate 9:1 (3 mL) followed by dichloromethane/methanol 9:1 (3 mL). The product containing fractions were was collected and concentrated in vacuo to give the final product.

General Procedure for the Preparation of Examples 120–121

A solution of methyl-3-(3-bromo-4-hydroxy-5-methoxyphenyl) cinnamate (0.14 mmol) (prepared according to Schreiber, F. G; Stevenson, R., J. *Chem. Soc., Perkin Trans.* 1, 1976, 14, 1514–18 and references cited therein) was coupled with the appropriate bromo compound (0.28 mmol benzylbromide or 2-(bromomethyl)-naphthalene) and hydrolyzed, using the procedure described for Examples 21–30 (Method C). This gave after purification on HPLC (using the same conditions as described for Examples 27, 28 and 30) the final products.

For a table of Examples 111–121 comprising yield and mass spectra, see Table below.

R—O—(aryl with $R_4$, Br)—CH=CH—$CO_2H$

| Example | R | $R_4$ | Yield (%) | $MS^1$ |
|---|---|---|---|---|
| 111 | 4-($F_3C$)-benzyl | Br | 35 | 478.9 |
| 112 | 2-Me-benzyl | Br | 34 | 424.9 |
| 113 | 3-($F_3C$O)-benzyl | Br | 58 | 495.1 |
| 114 | pyridin-2-ylmethyl | Br | 28 | 412.0 |
| 115 | quinolin-2-ylmethyl | Br | 10 | 461.8 |
| 116 | 3-($F_3C$)-5-F-benzyl | Br | 53 | 497.2 |
| 117 | 5-Me-isoxazol-3-ylmethyl | Br | 62 | 415.9 |
| 118 | 3-Br-benzyl | Br | 47 | 488.8 |
| 119 | naphthalen-2-ylmethyl | Br | 10 | 460.9 |

-continued

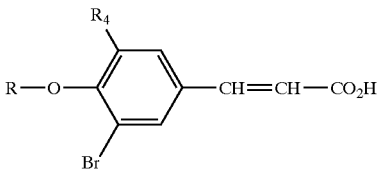

| Example | R | R₄ | Yield (%) | MS¹ |
|---|---|---|---|---|
| 120 | (Br-phenyl-CH₂) | OMe | 19 | 442.1 |
| 121 | (naphthyl-CH₂) | OMe | 6 | 413.3 |

The compounds of the invention exhibit binding affinities to the ThRa receptor in the range of 100 nM to 1000 nM.

What is claimed is:

1. Compounds with the general formula:

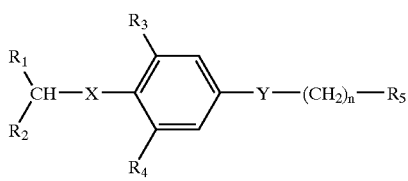

or pharmaceutically acceptable salts thereof, wherein:

$R_1$ is selected from: $C_{5-10}$ aryl; $C_{5-10}$ heteroaryl; and $C_{5-10}$ cycloalkyl; said aryl, heteroaryl, cycloalkyl optionally being substituted with 1 to 3 groups of $R^a$;

$R_2$ is selected from: hydrogen; $C_{1-4}$ alkyl; $C_{2-4}$ alkenyl; $C_{2-4}$ alkynyl and $C_{1-4}$ alkoxy;

$R_1$ may be linked through the available carbons to $R_2$, thus forming a $C_4$–$C_8$ cycloalkyl, saturated or partially unsaturated, and optionally substituted with 1 to 3 groups of $R^a$;

X is selected from the group consisting of: —O—; —S—; and Se—; $R_3$ and $R_4$ are the same or different and are selected from:

halogen; $C_{1-4}$ alkyl; $C_{3-7}$ cycloalkyl; $C_{2-4}$ alkenyl; $C_{2-4}$ alkynyl; $C_{1-4}$ alkoxy; —CF₃; —OCF₃; —OCF₂H; —SCH₃; —SCF₃; and COOH;

with the proviso that when $R_3$ is $C_{1-4}$ alkoxy; —OCF₃; OCF₂H;

—SCH₃; —SCF₃; or —COOH, then $R_4$ must be selected from:

halogen; $C_{1-4}$ alkyl; $C_{2-4}$ alkenyl; $C_{2-4}$ alkynyl; $C_{3-7}$ cycloalkyl; and —CF₃;

n is an integer of 0, 1, 2 or 3;

Y is selected from the group consisting of: —CO—; —O—; —S—; —CH₂— and —N(R$^c$)— with the proviso that when Y is —N(R$^c$)—, $R_5$ is not a carboxylic acid (—CO₂H), and with the further proviso that when Y is —CH₂—, n is not zero;

$R_5$ is independently selected from:
carboxylic acid (—CO₂H);
phosphonic acid (—PO(OH)₂);
phosphamic acid (—PO(OH)NH₂);
sulphonic acid (—SO₂OH);
α-keto carboxylic acid (COCO₂H);
sulphonamide (—SO₂NHR');
sulphonamide (—NHSO₂R'), with the proviso that then Y is CO and n is 0;
acylsulphonamide (—CONHSO₂R') or (—SO₂NHCOR'); wherein R' is selected from the group consisting of phenyl, m-nitrophenyl, p-nitrophenyl, and methyl;

$R^a$ represents a member selected from: hydrogen; halogen; CF₃; $C_{1-4}$ alkyl; $C_{2-4}$ alkenyl; $C_{2-4}$ alkynyl; $C_{1-4}$ alkoxy; —SMe; —CN; —NO₂; and —N(C$_{0-4}$)₂;

$R^c$ represents a member selected from: hydrogen; $C_{1-4}$ alkyl; $C_{3-4}$ alkenyl; and $C_{3-4}$ alkynyl;

included for the variables above are all the possible stereoisomers thereof.

2. The compounds according to claim 1 wherein:
X is —O—; and other variables are kept as in claim 1.

3. The compounds according to claim 1 wherein:
$R_2$ is selected from hydrogen and methyl;
X is —O—;
$R_3$ and $R_4$ are the same or different and are halogen, $C_{1-4}$ alkyl, $C_{2-4}$ alkenyl; $C_{2-4}$ alkynyl, or —CF₃;
n is 1;
y is —CH₂—;
$R_5$ is a carboxylic acid (—CO₂H); and
other variables are kept as described in claim 1.

4. The compounds according to claim 1 wherein:
X is —O—;
Y is —N(R$^c$)—;
n is an integer of 0, 1 and 2;
$R_5$ is an α-keto carboxylic acid (COCO₂H);
$R^c$ is hydrogen; and
other variables kept as described in claim 1.

5. The compounds according to claim 1 wherein:
X is —O—;
Y is —O—;
n is an integer of 1 and 2;
$R_5$ is a carboxylic acid (—CO₂H); and
other variables kept as described in claim 1.

6. The compounds according to claim 1 wherein:
X is —O—;
Y is —CO—;
n is 0;
$R_5$ is a sulphonamide (—NHSO₂R'); and
other variables kept as described in claim 1.

7. The compounds according to claim 1 wherein:
$R_2$ is selected from hydrogen and methyl;
X is —O—;
$R_3$ is —COOH and $R_4$ is selected from: halogen; $C_{1-4}$ alkyl, $C_{2-4}$ alkenyl; $C_{2-4}$ alkynyl, and —CF₃;
$R^c$ is hydrogen; and
other variables kept as described in claim 1.

8. Compounds having the formulae selected from the group consisting of:

| R | n |
|---|---|
| cyclohexylmethyl | 1 |
| cyclohexylmethyl | 2 |
| cyclohexylpropyl | 2 |
| 3-methylbenzyl | 2 |
| benzyl | 2 |
| benzyl | 1 |
| 3-(trifluoromethyl)benzyl | 2 |
| 3-bromobenzyl | 2 |
| 2-methylbenzyl | 2 |
| 4-methylbenzyl | 2 |
| 3,5-dimethylbenzyl | 2 |
| 4-fluorobenzyl | 2 |
| 4-(trifluoromethyl)benzyl | 2 |
| 3-nitrobenzyl | 2 |
| 4-tert-butylbenzyl | 2 |

N-[3,5-Dibromo-4-(3-bromobenzyloxy)benzoyl]benzenesulphonamide;

N-[3,5-Dibromo-4-(3-bromobenzyloxy)benzoyl]-3-nitrobenzenesulphonamide;

N-[3,5-Dibromo-4-(3-bromobenzyloxy)benzoyl]-4-nitrobenzenesulphonamide;

4-Amino-N-[3,5-dibromo-4-(3-bromobenzyloxy)benzoyl]benzenesulphonamide;

N-[3,5-Dibromo-4-(3-bromobenzyloxy)benzoyl]methanesulphonamide;

and the compounds indicated in the table below;

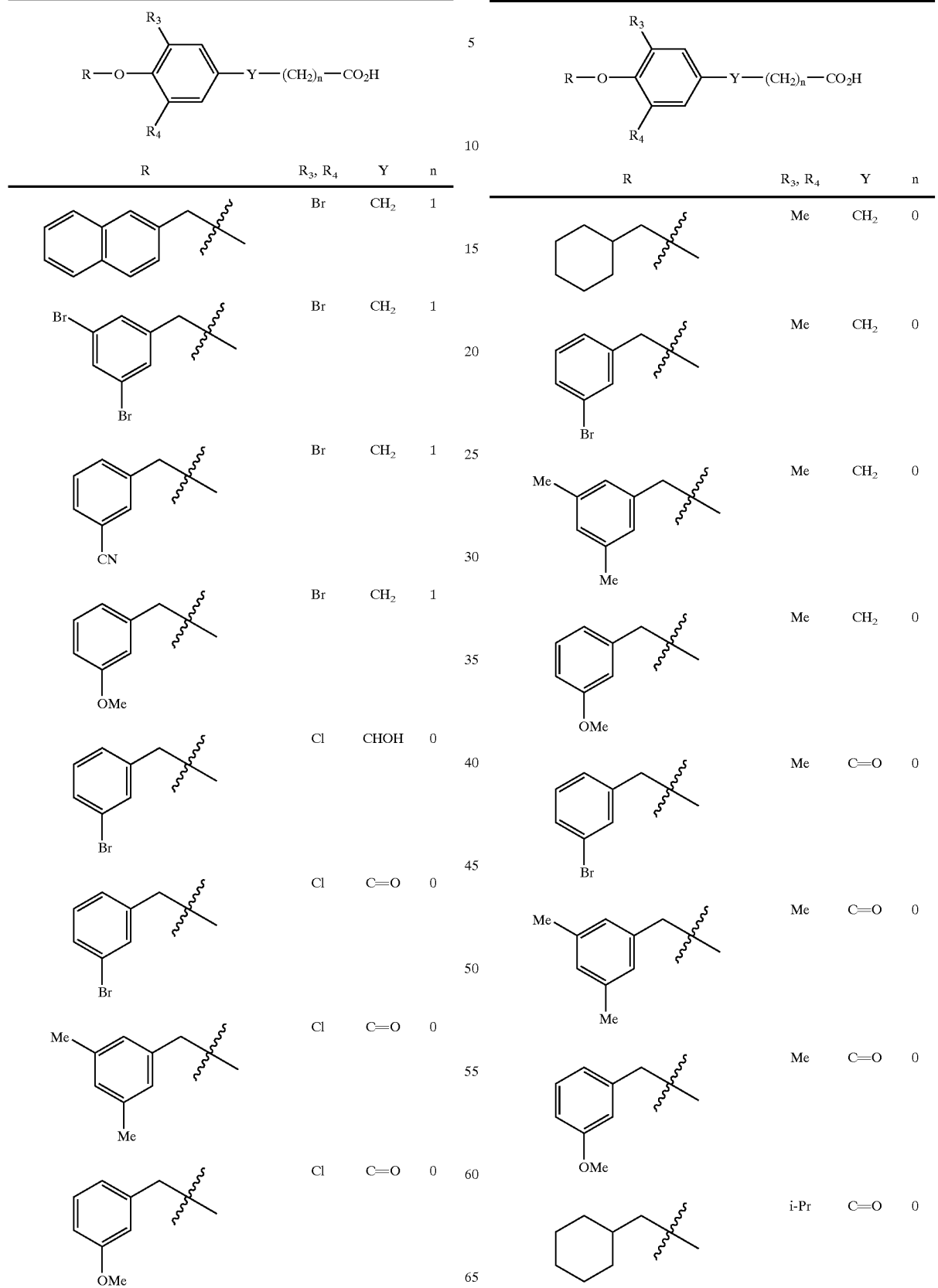

-continued structure
R—O—[phenyl with R3, R4]—Y—(CH2)n—CO2H

| R | R3, R4 | Y | n |
|---|---|---|---|
| 3-bromobenzyl | i-Pr | C=O | 0 |
| 3,5-dimethylbenzyl | i-Pr | C=O | 0 |
| 3-methoxybenzyl | i-Pr | C=O | 0 |
| 3-bromobenzyl | i-Pr | CH2 | 0 |
| 3,5-dimethylbenzyl | i-Pr | CH2 | 0 |
| 3-methoxybenzyl | i-Pr | CH2 | 0 |
| 3-(trifluoromethoxy)benzyl | Br | CH2 | 1 |
| 3-(trifluoromethyl)-5-fluorobenzyl | Br | CH2 | 1 |

-continued

R—O—[phenyl with R3, R4]—Y—(CH2)n—CO2H

| R | R3, R4 | Y | n |
|---|---|---|---|
| 3-fluorobenzyl | Br | CH2 | 1 |
| 3,5-difluorobenzyl | Br | CH2 | 1 |
| 3,5-bis(trifluoromethyl)benzyl | Br | CH2 | 1 |
| 3-(difluoromethoxy)benzyl | Br | CH2 | 1 |
| naphthalen-1-ylmethyl | Br | CH2 | 1 |
| pyridin-2-ylmethyl | Br | CH2 | 1 |
| pyridin-3-ylmethyl | Br | CH2 | 1 |
| pyridin-4-ylmethyl | Br | CH2 | 1 |
| quinolin-2-ylmethyl | Br | CH2 | 1 |

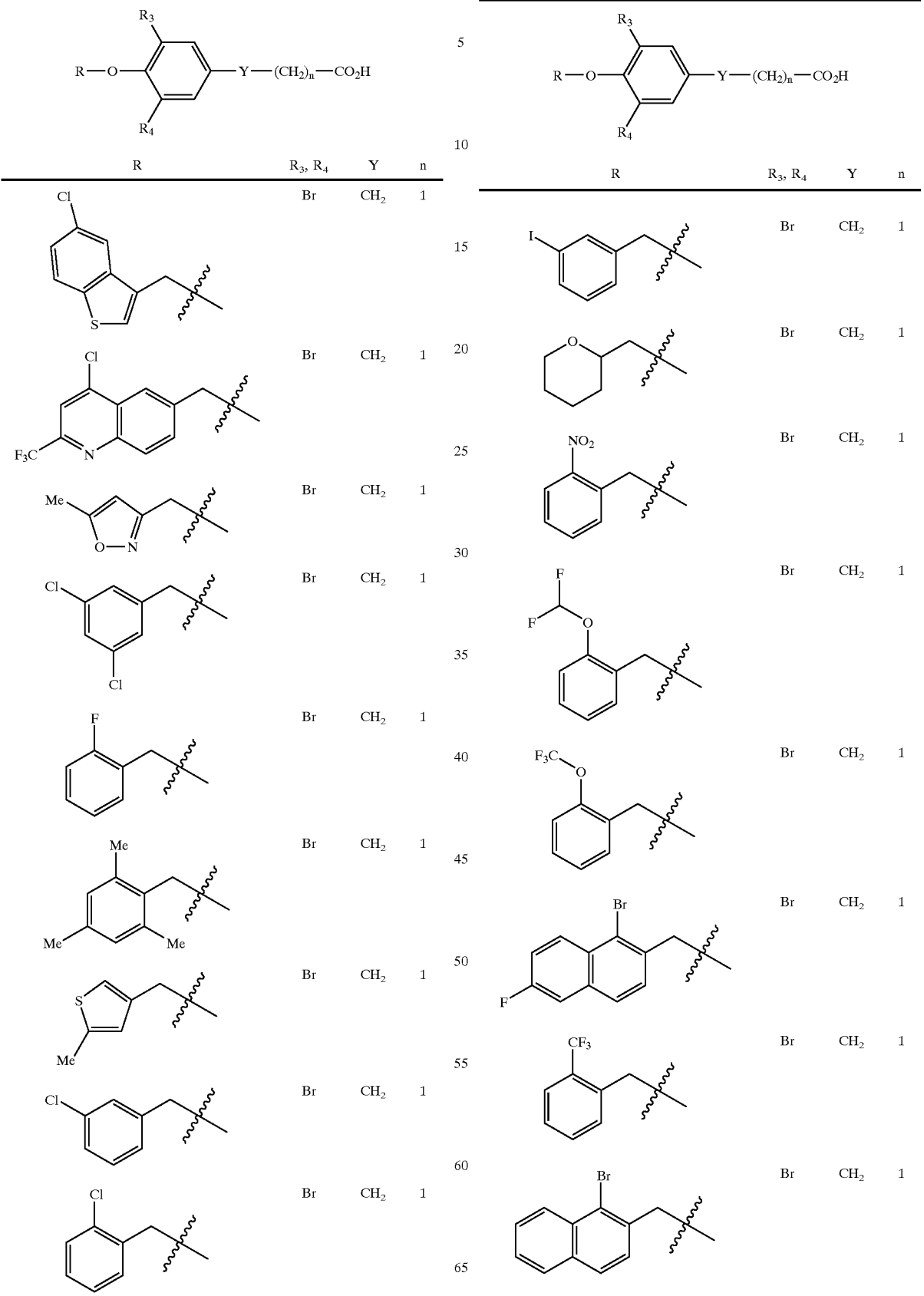

-continued

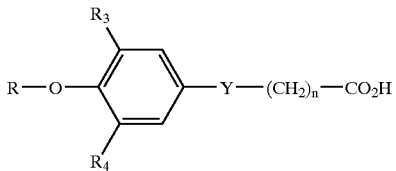

| R | R₃, R₄ | Y | n |
|---|---|---|---|
| 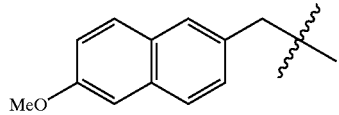 | Br | CH₂ | 1 |

3-[3,5-Dibromo-4-(3-ethoxybenzyloxy)phenyl]propionic acid;
3-[3,5-Dibromo-4-(3-propyloxybenzyloxy)phenyl]propionic acid;
3-[3,5-Dibromo-4-(3-butyloxybenzyloxy)phenyl]propionic acid;
3-[3,5-Dibromo-4-(3-aminobenzyloxy)phenyl]propionic acid;
3-[3,5-Dibromo-4-(3-ethylaminebenzyloxy)phenyl]propionic acid;
3-[3,5-Dibromo-4-(3-diethylaminebenzyloxy)phenyl]propionic acid;
N-[3,5-Dibromo-4-(3-bromobenzyloxy)phenyl]oxamic acid;
N-[3,5-Dibromo-4-(2-methylnaphthyloxy)phenyl]oxamic acid;
3-[3-bromo-5-methoxy-4-(3-bromobenzyloxy)phenyl]propionic acid;
3-[3-bromo-5-methoxy-4-(2-methylnaphthyloxy)phenyl]propionic acid;
and pharmaceutically acceptable salts thereof, and stereoisomers thereof.

9. A compound according to claim 1, which has one or more asymmetric centers and can exist in the form of racemates, single and multiple enantiomers, as individual diastereomers, with all possible isomers, and mixtures thereof.

10. A pharmaceutical composition comprising an effective amount of a compound according to claim 1 or a pharmaceutically effective salt thereof, together with a pharmaceutically acceptable carrier.

* * * * *